United States Patent
Howard et al.

(10) Patent No.: US 9,441,232 B2
(45) Date of Patent: Sep. 13, 2016

(54) PERICARP TISSUE PREFERRED REGULATORY REGION AND METHOD OF USING SAME

(71) Applicant: Applied Biotechnology Institute, San Luis Obispo, CA (US)

(72) Inventors: John Howard, Cayucos, CA (US); Erin Engelkrout, San Luis Obispo, CA (US)

(73) Assignee: Applied Biotechnology Institute, Inc, San Luis Obispo, CA (US)

( * ) Notice: Subject to any disclaimer, the term of this patent is extended or adjusted under 35 U.S.C. 154(b) by 395 days.

(21) Appl. No.: 13/788,731

(22) Filed: Mar. 7, 2013

(65) Prior Publication Data

US 2013/0305413 A1    Nov. 14, 2013

Related U.S. Application Data

(60) Provisional application No. 61/644,333, filed on May 8, 2012.

(51) Int. Cl.
*C12N 15/82* (2006.01)
*C07K 14/425* (2006.01)

(52) U.S. Cl.
CPC ......... *C12N 15/8234* (2013.01); *C07K 14/425* (2013.01); *C12N 15/8241* (2013.01); *C12N 15/8257* (2013.01)

(58) Field of Classification Search
None
See application file for complete search history.

(56) References Cited

U.S. PATENT DOCUMENTS

| | | | | |
|---|---|---|---|---|
| 5,608,152 | A * | 3/1997 | Kridl et al. | .......... 800/306 |
| 7,897,746 | B2 | 3/2011 | Abbitt et al. | |
| 2011/0010801 | A1 | 1/2011 | Abbitt et al. | |

OTHER PUBLICATIONS

Shaner et al, Nat Meth 9(19):905-09 (2005).*
Song et al., AF090447 (2003).*
Song et al., Genom Res 11:1817-25 (2001).*
Potenza et al., In Vitro Cell Dev Biol Plant 40:1-22 (2004).*
Donald & Cashmore, EMBO J 9:1717-26 (1990).*
Kim et al., Plant Mol Biol 24:105-17 (1994).*
Dolferus et al., Plant Physiol 105:1075-87 (1994).*
El-Mezawy A., Wu L., Shah S., 2009, "A Seed Coat-Specific Promoter for Canola", Tiotechnol Lett 31, 12, 1961-1965. Doi:10.107/s10529-009-0098-y.
Feng L., et al al., 2009, "Expressional Profiling Study Revealed Unique Expressional Patterns and Dramatic Expressional Divergence of Maize a-zein Super Gene Family", Plant Mol Bio 69, 6, 649659. Doi:10.1007/s11103-008-9444-z.
Locatelli, S., Piatti P., Motto M., Rossi V., 2009, "Chromatin and DNA Modifications in the Opaque2-Mediated Regulation of Gene Transcription During Maize Endosperm Development", Plant Cell Online 21 (5):1410-1427. Doi:10.1105/tpc.109.067256.
Miclaus M., Xu JH, Messing J., 2011, "Differential Gene Expression and Epiregulation of Alpha Zein Gene Copies in Maize Haplotypes", PLoS Genet 7 (6):e1002131. Doi:10.1371/journal.pgen.1002131.
Muhitch MJ, Liang H., Rastogi R., Sollenb ert KG, 2002, "Isolation of a Promoter Sequence From the Glutamine Synthetase (1-2) Gene Capable of Conferring Tissue-Specific Gene Expression in Transgenic Maize", Plant Sci 163 (4):865-872. Doi:10.1016/S0168-9452(02)00235-2.
Song RT, Llaca V., Linton E., Messing J., 2001, "Sequence, Regulation, and Evolution of the Maize 22-kD a-zein in Gene Family". Genome Res 11:1817-1825. Doi:10.1101/gr.197301.
Song RT, Messing J., 2003, "Gene Expression of a Gene Family in Maize Based on Noncollinear Haplotypes", Proc Natl Acad Sci USA, 100 (15):9055-9060. Doi:10.1073/pnas. 1032999100.
Woo, et al., 2001, "Genomics Analysis of Genes Expressed in Maize Endosperm Identifies Novel Seed Proteins and Clarifies Patterns of Zein Gene Expression", Plant Cell, 13:2297-2317.
Wu L, El-Mezaway A., Duong M., Shah S., 2010, "Two Seed Coat-Specific Promoters are Functionally Conserved Between Arabidopsis thaliana and BrasicA napus", In Vitro Cell Dev—PI 46 (4):338-347. Doi:10.1007/s11627-010-9277-8.
Wu L, El-Mezawy A., Shah S., 2011, "A Seed Coat Outer Integument-Specific Promoter for BrassicA napus", Plant Cell Rep. 30 (1):75-80. Doi:10.1007/s00299-010-0945-2.
Song et al. GenBank AF090447.2 (1998).
Llaca et al. GenBank AF031569 (1997).
Lai et al. GenBank BT016832.1 (2004).
Kridl et al. GenBank K02066 (1984).
Thompson et al. GenBank X61085, (2005).
Schnable et al. NCBI Ref NM_001111589.1 (2001).
Larkins et al. (1984) the zein proteins of maize endosperm: TIBS pp. 306-308.

* cited by examiner

*Primary Examiner* — David H Kruse
*Assistant Examiner* — Russell Boggs
(74) *Attorney, Agent, or Firm* — Patricia A. Sweeney

(57) ABSTRACT

A *Zea mays* regulatory region is shown, which provides improved seed preferred, and particularly pericarp preferred expression in plants. Methods of use are also shown in preferentially expressing a heterologous protein to the pericarp tissue of a plant. The sequence is particularly useful in expression of heterologous proteins to the pericarp of monocotyledonous plants, particularly cereals, and maize.

15 Claims, 4 Drawing Sheets

Figure 1

PMD – 22 kDa alpha zein ctagctttacatcaaattgaataaagaacgacagttcaacatatactccatccacactagtttattacgtgtcctagcttttc
cctaaattagtttccctaaatttacataattcttagaaattgtatccatattttgaagatcaaatttcttccaatgagttattta
tgacatatatattggtattgcattttagtcatcaaaatatatttagaactctaacaaagctatacatgattcgttaaagaca
atacccaagaaaattgtaatcaagaatactctagatgtgtgccaattgccacgtttacataaaatcattctaactttgttca
tcctatgtttgtgcattcatctatgcatttaggattacaattagtctcaatcttgtagtaattttcattcatagtttgatcagtt
ctcgtctatctactatgcttgttcaaccacgagaagaatattaggacaatatccatttataaacgctttgatagcaaacttt
acatattcatcatgtcggtaaaatggaacatttatgatgtggttaaggttgtcgcatgtgtaaaggtgaagagatgatgca
tgtcatccaagtatatgaaaagaattcctatagaaaatgacaattttcttgtaggtaatggaaactagctttccagcaaa
gaccatataatctgatgaaactgataaccaaatgtcgaaattgagtaggtgccatatcattgatagcttatctattgtttgg
caaaaagataaaatccaaatatatatatatgagatctcaccta<u>atataaat</u>atctcccaaatcagtagttaatcc*atcgcccata
atattttgagcattcaaaaacacacaaagggaagtgcactagcaacttcctaacaacc*ATG 9071 (zein+native 5'UTR:GUS)

SEQUENCE LISTING

```
<160> NUMBER OF SEQ ID NOS: 12

<210> SEQ ID NO 1
<211> LENGTH: 787
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 1

```
ctagctttac atcaaattga ataaagaacg acagttcaac atatactcca tccacactag      60
tttattacgt gtcctagctt ttccctaaat tagtttccct aaatttacat aattcttaga     120
aattgtatcc atattttgaa gatcaaattt cttccaatga gttatttatg acatatatat     180
tggtattgca ttttagtcat caaatatat ttagaactct aacaaagcta tacatgattc      240
gttaaagaca atacccaaga aaattgtaat caagaatact ctagatgtgt gccaattgcc     300
acgtttacat aaaatcattc taactttgtt catcctatgt ttgtgcattc atctatgcat     360
ttaggattac aattagtctc aatcttgtag taattttca ttcatagttt gatcagttct      420
cgtctatcta ctatgcttgt tcaaccacga gaagaatatt aggacaatat ccatttataa     480
acgctttgat agcaaacttt acatattcat catgtcggta aaatggaaca tttatgatgt     540
ggttaaggtt gtcgcatgtg taaaggtgaa gagatgatgc atgtcatcca agtatatgaa     600
aagaattcct atagaaaatg acaattttc ttgtaggtaa tggaaactag ctttccagca      660
aagaccatat aatctgatga aactgataac caaatgtcga aattgagtag gtgccatatc     720
attgatagct tatctattgt ttggcaaaaa gataaaatcc aaatatatat atatgagatc     780
tcaccta                                                              787
```

<210> SEQ ID NO 2
<211> LENGTH: 884
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 2

```
ctagctttac atcaaattga ataaagaacg acagttcaac atatactcca tccacactag      60
tttattacgt gtcctagctt ttccctaaat tagtttccct aaatttacat aattcttaga     120
aattgtatcc atattttgaa gatcaaattt cttccaatga gttatttatg acatatatat     180
tggtattgca ttttagtcat caaatatat ttagaactct aacaaagcta tacatgattc      240
gttaaagaca atacccaaga aaattgtaat caagaatact ctagatgtgt gccaattgcc     300
acgtttacat aaaatcattc taactttgtt catcctatgt ttgtgcattc atctatgcat     360
ttaggattac aattagtctc aatcttgtag taattttca ttcatagttt gatcagttct      420
cgtctatcta ctatgcttgt tcaaccacga gaagaatatt aggacaatat ccatttataa     480
acgctttgat agcaaacttt acatattcat catgtcggta aaatggaaca tttatgatgt     540
ggttaaggtt gtcgcatgtg taaaggtgaa gagatgatgc atgtcatcca agtatatgaa     600
aagaattcct atagaaaatg acaattttc ttgtaggtaa tggaaactag ctttccagca      660
aagaccatat aatctgatga aactgataac caaatgtcga aattgagtag gtgccatatc     720
attgatagct tatctattgt ttggcaaaaa gataaaatcc aaatatatat atatgagatc     780
tcacctatat aaatatctcc caaatcagta gttaatccat cgcccataat attttgagca     840
ttcaaaaaca cacaaaggga agtgcactag caacttccta acaa                     884
```

<210> SEQ ID NO 3
<211> LENGTH: 889
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3

```
ctagctttac atcaaattga ataaagaacg acagttcaac atatactcca tccacactag      60
tttattacgt gtcctagctt ttccctaaat tagtttccct aaatttacat aattcttaga     120
aattgtatcc atattttgaa gatcaaattt cttccaatga gttatttatg acatatatat     180
tggtattgca ttttagtcat caaaatatat ttagaactct aacaaagcta tacatgattc     240
gttaaagaca atacccaaga aaattgtaat caagaatact ctagatgtgt gccaattgcc     300
acgtttacat aaaatcattc taactttgtt catcctatgt tgtgcattc atctatgcat      360
ttaggattac aattagtctc aatcttgtag taattttca ttcatagttt gatcagttct      420
cgtctatcta ctatgcttgt tcaaccacga aagaatatt aggacaatat ccatttataa      480
acgctttgat agcaaacttt acatattcat catgtcggta aaatggaaca tttatgatgt     540
ggttaaggtt gtcgcatgtg taaaggtgaa gagatgatgc atgtcatcca agtatatgaa     600
aagaattcct atagaaaatg acaatttttc ttgtaggtaa tggaaactag ctttccagca     660
aagaccatat aatctgatga aactgataac caaatgtcga aattgagtag gtgccatatc     720
attgatagct tatctattgt ttggcaaaaa gataaaatcc aaatatatat atatgagatc     780
tcacctatat aaatatctcc caaatcagta gttaatccat cgcccataat attttgagca     840
ttcaaaaaca cacaaaggga agtgcactag caacttccta acaaccatg                 889
```

<210> SEQ ID NO 4
<211> LENGTH: 866
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 4

```
ctagctttac atcaaattga ataaagaacg acagttcaac atatactcca tccacactag      60
tttattacgt gtcctagctt ttccctaaat tagtttccct aaatttacat aattcttaga     120
aattgtatcc atattttgaa gatcaaattt cttccaatga gttatttatg acatatatat     180
tggtattgca ttttagtcat caaaatatat ttagaactct aacaaagcta tacatgattg     240
cttaaagaca atacccgaag aaaattgtaa tcaagaatac tctagatgtg tgccaattgc     300
cacgtttaca taaaatcatt ctaactttgt tcatcctatg tttgtgcatt catctatgca     360
tttaggatta caattagtct caatcttgta gtaattttc attcatagtt tgatcagttc      420
tcgtctatct actatgcttg ttcaaccacg agaagaatat tagacaatat ccatttataa     480
acgctttgat agcaaacttt acatattcat catgtcggta aaatggaaca tttatgatgt     540
ggttaaggtt gtcgcatgtg taaaggtgaa gagatgatgc atgtcatcca agtatatgaa     600
aagaattcct atagaaaatg acaatttttc ttgtaggtaa tggaaactag ctttccagca     660
aagaccatat aatctgatga aactgataac caaatgtcga aattgagtag gtgccatatc     720
attgatagct tatctattgt ttggcaaaaa gataaaatcc aaatatatat atatgagatc     780
tcacctatat aaatatctcc caaatcagta gttaatccat cgcccataat attttgagca     840
ttcaaaaaca cacaaaggga agtgca                                         866
```

<210> SEQ ID NO 5
<211> LENGTH: 68
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 5
atcgcccata atattttgag cattcaaaaa cacacaaagg gaagtgcact agcaacttcc      60
taacaacc                                                              68

<210> SEQ ID NO 6
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
atcgcccata atattttgag cattcaaaaa cacacaaagg gaagtgca                   48

<210> SEQ ID NO 7
<211> LENGTH: 886
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
ctagctttac atcaaattga ataaagaacg acagttcaac atatactcca tccacactag      60
tttattacgt gtcctagctt ttccctaaat tagtttccct aaatttacat aattcttaga     120
aattgtatcc atattttgaa gatcaaattt cttccaatga gttatttatg acatatatat     180
tggtattgca ttttagtcat caaaatatat ttagaactct aacaaagcta tacatgattc     240
gttaaagaca atacccaaga aaattgtaat caagaatact ctagatgtgt gccaattgcc     300
acgtttacat aaaatcattc taactttgtt catcctatgt ttgtgcattc atctatgcat     360
ttaggattac aattagtctc aatcttgtag taatttttca ttcatagttt gatcagttct     420
cgtctatcta ctatgcttgt tcaaccacga gaagaatatt aggacaatat ccatttataa     480
acgctttgat agcaaacttt acatattcat catgtcggta aaatggaaca tttatgatgt     540
ggttaaggtt gtcgcatgtg taaaggtgaa gagatgatgc atgtcatcca agtatatgaa     600 agaattcct atagaaaatg acaattttc ttgtaggtaa tggaaactag ctttccagca      660
aagaccatat aatctgatga aactgataac caaatgtcga aattgagtag gtgccatatc     720
attgatagct tatctattgt ttggcaaaaa gataaaatcc aaatatatat atatgagatc     780
tcacctatat aaatatctcc caaatcagta gttaatccat cgcccataat attttgagca     840
ttcaaaaaca cacaagggga agtgcactag caacttccta acaacc                   886

<210> SEQ ID NO 8
<211> LENGTH: 787
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
ctagctttac atcaaattga ataaagaacg acagttcaac atatactcca tccacactag      60
tttattacgt gtcctagctt ttccctaaat tagtttccct aaatttacat aattcttaga     120
```

| | |
|---|---|
| aattgtatcc atattttgaa gatcaaattt cttccaatga gttatttatg acatatatat | 180 |
| tggtattgca ttttagtcat caaaatatat ttagaactct aacaaagcta tacatgattg | 240 |
| cttaaagaca atacccgaag aaaattgtaa tcaagaatac tctagatgtg tgccaattgc | 300 |
| cacgtttaca taaatcatt ctaactttgt tcatcctatg tttgtgcatt catctatgca | 360 |
| tttaggatta caattagtct caatcttgta gtaattttc attcatagtt tgatcagttc | 420 |
| tcgtctatct actatgcttg ttcaaccacg agaagaatat tagacaatat ccatttataa | 480 |
| acgctttgat agcaaacttt acatattcat catgtcggta aaatggaaca tttatgatgt | 540 |
| ggttaaggtt gtcgcatgtg taaaggtgaa gagatgatgc atgtcatcca agtatatgaa | 600 |
| aagaattcct atagaaaatg acaatttttc ttgtaggtaa tggaaactag ctttccagca | 660 |
| aagaccatat aatctgatga aactgataac caaatgtcga attgagtag gtgccatatc | 720 |
| attgatagct tatctattgt ttggcaaaaa gataaaatcc aaatatatat atatgagatc | 780 |
| tcaccta | 787 |

<210> SEQ ID NO 9
<211> LENGTH: 10768
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 9

| | |
|---|---|
| gtttacccgc caatatatcc tgtcaaacac tgatagttta aactgaaggc gggaaacgac | 60 |
| aatctgatca tgagcggaga attaagggag tcacgttatg accccgccg atgacgcggg | 120 |
| acaagccgtt ttacgtttgg aactgacaga accgcaacgt tgaaggagcc actcagcaag | 180 |
| ctacctagga tgtgactaga ccggtgatcg tgatcggcgc gccaagcttc tagctttaca | 240 |
| tcaaattgaa taaagaacga cagttcaaca tatactccat ccacactagt ttattacgtg | 300 |
| tcctagcttt tccctaaatt agtttcccta aatttacata attcttagaa attgtatcca | 360 |
| tattttgaag atcaaatttc ttccaatgag ttatttatga catatatatt ggtattgcat | 420 |
| tttagtcatc aaaatatatt tagaactcta acaaagctta acatgattcg ttaaagacaa | 480 |
| tacccaagaa aattgtaatc aagaatactc tagatgtgtg ccaattgcca cgtttacata | 540 |
| aaatcattct aactttgttc atcctatgtt tgtgcattca tctatgcatt taggattaca | 600 |
| attagtctca atcttgtagt aattttttcat tcatagtttg atcagttctc gtctatctac | 660 |
| tatgcttgtt caaccacgag aagaatatta ggacaatatc catttataaa cgctttgata | 720 |
| gcaaaccttta catattcatc atgtcggtaa aatggaacat ttatgatgtg gttaaggttg | 780 |
| tcgcatgtgt aaaggtgaag agatgatgca tgtcatccaa gtatatgaaa agaattccta | 840 |
| tagaaaatga caatttttct tgtaggtaat ggaaactagc tttccagcaa agaccatata | 900 |
| atctgatgaa actgataacc aaatgtcgaa attgagtagg tgccatatca ttgatagctt | 960 |
| atctattgtt tggcaaaaag ataaaatcca aatatatata tatgagatct cacctatata | 1020 |
| aatatctccc aaatcagtag ttaatccatc gcccataata ttttgagcat tcaaaaacac | 1080 |
| acaagggaa gtgcactagc aacttcctaa caaccatggt ccgtcctgta gaaaccccaa | 1140 |
| cccgtgaaat caaaaaactc gacggcctgt gggcattcag tctggatcgc gaaaactgtg | 1200 |
| gaattgatca gcgttggtgg gaaagcgcgt tacaagaaag ccgggcaatt gctgtgccag | 1260 |
| gcagttttaa cgatcagttc gccgatgcag atattcgtaa ttatgcgggc aacgtctggt | 1320 |

```
atcagcgcga agtctttata ccgaaaggtt gggcaggcca gcgtatcgtg ctgcgtttcg    1380
atgcggtcac tcattacggc aaagtgtggg tcaataatca ggaagtgatg gagcatcagg    1440
gcggctatac gccatttgaa gccgatgtca cgccgtatgt tattgccggg aaaagtgtac    1500
gtatcaccgt ttgtgtgaac aacgaactga actggcagac tatcccgccg ggaatggtga    1560
ttaccgacga aaacggcaag aaaaagcagt cttacttcca tgatttcttt aactatgccg    1620
gaatccatcg cagcgtaatg ctctacacca cgccgaacac ctgggtggac gatatcaccg    1680
tggtgacgca tgtcgcgcaa gactgtaacc acgcgtctgt tgactgccag gtggtggcca    1740
atggtgatgt cagcgttgaa ctgcgtgatg cggatcaaca ggtggttgca actggacaag    1800
gcactagcgg gactttgcaa gtggtgaatc cgcacctctg ccaaccgggt gaaggttatc    1860
tctatgaact gtgcgtcaca gccaaaagcc agacagagtg tgatatctac ccgcttcgcg    1920
tcggcatccg gtcagtggca gtgaagggcc aacagttcct gattaaccac aaaccgttct    1980
actttactgg ctttggtcgt catgaagatg cggacttacg tggcaaagga ttcgataacg    2040
tgctgatggt gcacgaccac gcattaatgg actggattgg ggccaactcc taccgtacct    2100
cgcattaccc ttacgctgaa gagatgctcg actgggcaga tgaacatggc atcgtggtga    2160
ttgatgaaac tgctgctgtc ggcttttaacc tctctttagg cattggtttc gaagcgggca    2220
acaagccgaa agaactgtac agcgaagagg cagtcaacgg ggaaactcag caagcgcact    2280
tacaggcgat taaagagctg atagcgcgtg acaaaaacca cccaagcgtg gtgatgtgga    2340
gtattgccaa cgaaccggat acccgtccgc aagtgcacgg gaatatttcg ccactggcgg    2400
aagcaacgcg taaactcgac ccgacgcgtc cgatcacctg cgtcaatgta atgttctgcg    2460
acgctcacac cgataccatc agcgatctct ttgatgtgct gtgcctgaac cgttattacg    2520
gatggtatgt ccaaagcggc gatttggaaa cggcagagaa ggtactggaa aaagaacttc    2580
tggcctggca ggagaaactg catcagccga ttatcatcac cgaatacggc gtggatacgt    2640
tagccgggct gcactcaatg tacaccgaca tgtggagtga agagtatcag tgtgcatggc    2700
tggatatgta tcaccgcgtc tttgatcgcg tcagcgccgt cgtcggtgaa caggtatgga    2760
atttcgccga ttttgcgacc tcgcaaggca tattgcgcgt tggcggtaac aagaaaggga    2820
tcttcactcg cgaccgcaaa ccgaagtcgg cggcttttct gctgcaaaaa cgctggactg    2880
gcatgaactt cggtgaaaaa ccgcagcagg gaggcaaaca acaccatcac catcaccatt    2940
gatgagttaa cctagacttg tccatcttct ggattggcca acttaattaa tgtatgaaat    3000
aaaaggatgc acacatagtg acatgctaat cactataatg tgggcatcaa agttgtgtgt    3060
tatgtgtaat tactagttat ctgaataaaa gagaaagaga tcatccatat ttcttatcct    3120
aaatgaatgt cacgtgtctt tataattctt tgatgaacca gatgcatttc attaaccaaa    3180
tccatataca tataaatatt aatcatatat aattaatatc aattgggtta gcaaaacaaa    3240
tctagtctag gtgtgttttg cgaatgcggc cgcacgcgtg atagtgatac gccggcgatg    3300
tcagtatgct agcggggccg cggaccgaat tcccatggag tcaaagattc aaatagagga    3360
cctaacagaa ctcgccgtaa agactggcga acagttcata cagagtctct tacgactcaa    3420
tgacaagaag aaaatcttcg tcaacatggt ggagcacgac acgcttgtct actccaaaaa    3480
tatcaaagat acagtctcag aagaccaaag ggcaattgag acttttcaac aaagggtaat    3540
atccggaaac ctcctcggat tccattgccc agctatctgt cactttattg tgaagatagt    3600
ggaaaaggaa ggtggctcct acaaatgcca tcattgcgat aaaggaaagg ccatcgttga    3660
agatgcctct gccgacagtg gtcccaaaga tggacccccca cccacgagga gcatcgtgga    3720
```

```
aaaagaagac gttccaacca cgtcttcaaa gcaagtggat tgatgtgata tctccactga   3780
cgtaagggat gacgcacaat cccactatcc ttcgcaagac ccttcctcta tataaggaag   3840
ttcatttcat ttggagagga cagggtaccc ggggatccac acgacaccat gtcccccgag   3900
cgccgccccg tcgagatccg cccggccacc gccgccgaca tggccgccgt gtgcgacatc   3960
gtgaaccact acatcgagac ctccaccgtg aacttccgca ccgagccgca gaccccgcag   4020
gagtggatcg acgacctgga gcgcctccag gaccgctacc cgtggctcgt ggccgaggtg   4080
gagggcgtgg tggccggcat cgcctacgcc ggcccgtgga aggcccgcaa cgcctacgac   4140
tggaccgtga gtccaccgt gtacgtgtcc caccgccacc agcgcctcgg cctcggctcc   4200
accctctaca cccacctcct caagagcatg gaggcccagg gcttcaagtc cgtggtggcc   4260
gtgatcggcc tcccgaacga cccgtccgtg cgcctccacg aggccctcgg ctacaccgcc   4320
cgcggcaccc tccgcgccgc cggctacaag cacggcggct ggcacgacgt cggcttctgg   4380
cagcgcgact cgagctgcc ggccccgccg cgccccggtgc cccggtgac gcagatctga   4440 gtcgacctgc aggcatgccc gctgaaatca ccagtctctc tctacaaatc tatctctctc   4500
tataataatg tgtgagtagt tcccagataa gggaattagg gttcttatag ggtttcgctc   4560
atgtgttgag catataagaa acccttagta tgtatttgta tttgtaaaat acttctatca   4620
ataaaatttc taattcctaa aaccaaaatc caggcgagc tcgaattcag tacattaaaa   4680
acgtccgcaa tgtgttatta agttgtctaa gcgtcaattt gtttacacca caatatatcc   4740
tgccaccagc cagccaacag ctccccgacc ggcagctcgg cacaaaatca ccactcgata   4800
caggcagccc atcagtccgg gacggcgtca gcgggagagc cgttgtaagg cggcagactt   4860
tgctcatgtt accgatgcta ttcggaagaa cggcaactaa gctgccgggt ttgaaacacg   4920
gatgatctcg cggagggtag catgttgatt gtaacgatga cagagcgttg ctgcctgtga   4980
tcaaatatca tctccctcgc agagatccga attatcagcc ttcttattca tttctcgctt   5040
aaccgtgaca ggctgtcgat cttgagaact atgccgacat aataggaaat cgctggataa   5100
agccgctgag gaagctgagt ggcgctattt ctttagaagt gaacgttgac gatcgtcgac   5160
cgtaccccga tgaattaatt cggacgtacg ttctgaacac agctggatac ttacttgggc   5220
gattgtcata catgacatca acaatgtacc cgtttgtgta accgtctctt ggaggttcgt   5280
atgacactag tggttcccct cagcttgcga ctagatgttg aggcctaaca ttttattaga   5340
gagcaggcta gttgcttaga tacatgatct tcaggccgtt atctgtcagg gcaagcgaaa   5400
attggccatt tatgacgacc aatgcccgc agaagctccc atctttgccg ccatagacgc   5460 cgcgccccc ttttggggtg tagaacatcc ttttgccaga tgtggaaaag aagttcgttg   5520
tcccattgtt ggcaatgacg tagtagccgg cgaaagtgcg agaccatttt gcgctatata   5580
taagcctacg atttccgttg cgactattgt cgtaattgga tgaactatta tcgtagttgc   5640
tctcagagtt gtcgtaattt gatggactat tgtcgtaatt gcttatggag ttgtcgtagt   5700
tgcttggaga aatgtcgtag ttggatgggg agtagtcata gggaagacga gcttcatcca   5760
ctaaaacaat tggcaggtca gcaagtgcct gccccgatgc catcgcaagt acgaggctta   5820
gaaccacctt caacagatcg cgcatagtct tccccagctc tctaacgctt gagttaagcc   5880
gcgccgcgaa gcggcgtcgg cttgaacgaa ttgttagaca ttatttgccg actaccttgg   5940
tgatctcgcc tttcacgtag tgaacaaatt cttccaactg atctgcgcgc gaggccaagc   6000
gatcttcttg tccaagataa gcctgcctag cttcaagtat gacgggctga tactgggccg   6060
```

-continued

```
gcaggcgctc cattgcccag tcggcagcga catccttcgg cgcgattttg ccggttactg    6120
cgctgtacca aatgcgggac aacgtaagca ctacatttcg ctcatcgcca gcccagtcgg    6180
gcggcgagtt ccatagcgtt aaggtttcat ttagcgcctc aaatagatcc tgttcaggaa    6240
ccggatcaaa gagttcctcc gccgctggac ctaccaaggc aacgctatgt tctcttgctt    6300
ttgtcagcaa gatagccaga tcaatgtcga tcgtggctgg ctcgaagata cctgcaagaa    6360
tgtcattgcg ctgccattct ccaaattgca gttcgcgctt agctggataa cgccacggaa    6420
tgatgtcgtc gtgcacaaca atggtgactt ctacagcgcg gagaatctcg ctctctccag    6480
gggaagccga agtttccaaa aggtcgttga tcaaagctcg ccgcgttgtt tcatcaagcc    6540
ttacggtcac cgtaaccagc aaatcaatat cactgtgtgg cttcaggccg ccatccactg    6600
cggagccgta caaatgtacg gccagcaacg tcggttcgag atggcgctcg atgacgccaa    6660
ctacctctga tagttgagtc gatacttcgg cgatcaccgc ttccctcatg atgtttaact    6720
cctgaattaa gccgcgccgc gaagcggtgt cggcttgaat gaattgttag gcgtcatcct    6780
gtgctcccga gaaccagtac cagtacatcg ctgtttcgtt cgagacttga ggtctagttt    6840
tatacgtgaa caggtcaatg ccgccgagag taaagccaca ttttgcgtac aaattgcagg    6900
caggtacatt gttcgtttgt gtctctaatc gtatgccaag gagctgtctg cttagtgccc    6960
acttttcgc aaattcgatg agactgtgcg cgactccttt gcctcggtgc gtgtgcgaca    7020
caacaatgtg ttcgatagag gctagatcgt tccatgttga gttgagttca atcttcccga    7080
caagctcttg gtcgatgaat gcgccatagc aagcagagtc ttcatcagag tcatcatccg    7140
agatgtaatc cttccggtag gggctcacac ttctggtaga tagttcaaag ccttggtcgg    7200
ataggtgcac atcgaacact tcacgaacaa tgaaatggtt ctcagcatcc aatgtttccg    7260
ccacctgctc agggatcacc gaaatcttca tatgacgcct aacgcctggc acagcggatc    7320
gcaaacctgg cgcggctttt ggcacaaaag gcgtgacagg tttgcgaatc cgttgctgcc    7380
acttgttaac ccttttgcca gatttggtaa ctataattta tgttagaggc gaagtcttgg    7440
gtaaaaactg gcctaaaatt gctggggatt tcaggaaagt aaacatcacc ttccggctcg    7500
atgtctattg tagatatatg tagtgtatct acttgatcgg gggatctgct gcctcgcgcg    7560
tttcggtgat gacggtgaaa acctctgaca catgcagctc ccggagacgg tcacagcttg    7620
tctgtaagcg gatgccggga gcagacaagc ccgtcagggc gcgtcagcgg gtgttggcgg    7680
gtgtcgggc gcagccatga cccagtcacg tagcgatagc ggagtgtata ctggcttaac    7740
tatgcggcat cagagcagat tgtactgaga gtgcaccata tgcggtgtga ataccgcac    7800
agatgcgtaa ggagaaaata ccgcatcagg cgctcttccg cttcctcgct cactgactcg    7860
ctgcgctcgg tcgttcggct gcggcgagcg gtatcagctc actcaaaggc ggtaatacgg    7920
ttatccacag aatcagggga taacgcagga agaacatgt gagcaaaagg ccagcaaaag    7980
gccaggaacc gtaaaaaggc cgcgttgctg gcgtttttcc ataggctccg ccccctgac    8040
gagcatcaca aaaatcgacg ctcaagtcag aggtggcgaa acccgacagg actataaaga    8100
taccaggcgt ttccccctgg aagctccctc gtgcgctctc ctgttccgac cctgccgctt    8160
accggatacc tgtccgcctt tctcccttcg ggaagcgtgg cgctttctca tagctcacgc    8220
tgtaggtatc tcagttcggt gtaggtcgtt cgctccaagc tgggctgtgt gcacgaaccc    8280
cccgttcagc ccgaccgctg cgccttatcc ggtaactatc gtcttgagtc aacccggta    8340
agacacgact tatcgccact ggcagcagcc actggtaaca ggattagcag agcgaggtat    8400
gtaggcggtg ctacagagtt cttgaagtgg tggcctaact acggctacac tagaaggaca    8460
```

```
gtatttggta tctgcgctct gctgaagcca gttaccttcg aaaaagagt tggtagctct    8520 tgatccggca aacaaccac cgctggtagc ggtggttttt ttgtttgcaa gcagcagatt    8580
acgcgcagaa aaaaggatc tcaagaagat cctttgatct tttctacggg gtctgacgct    8640
cagtggaacg aaaactcacg ttaagggatt ttggtcatga gattatcaaa aaggatcttc    8700
acctagatcc ttttaaatta aaaatgaagt tttaaatcaa tctaaagtat atatgagtaa    8760
acttggtctg acagttacca atgcttaatc agtgaggcac ctatctcagc gatctgtcta    8820
tttcgttcat ccatagttgc ctgactcccc gtcgtgtaga taactacgat acgggagggc    8880
ttaccatctg gccccagtgc tgcaatgata ccgcgagacc cacgctcacc ggctccagat    8940
ttatcagcaa taaaccagcc agccggaagg gccgagcgca gaagtggtcc tgcaacttta    9000
tccgcctcca tccagtctat taattgttgc cgggaagcta gagtaagtag ttcgccagtt    9060
aatagtttgc gcaacgttgt tgccattgct gcaggggggg ggggggggg ggacttccat    9120 tgttcattcc acggacaaaa acagagaaag gaaacgacag aggccaaaaa gcctcgcttt    9180
cagcacctgt cgtttccttt cttttcagag ggtattttaa ataaaaacat taagttatga    9240
cgaagaagaa cggaaacgcc ttaaaccgga aaattttcat aaatagcgaa acccgcgag    9300 gtcgccgccc cgtaacctgt cggatcaccg gaaaggaccc gtaaagtgat aatgattatc    9360
atctacatat cacaacgtgc gtggaggcca tcaaaccacg tcaaataatc aattatgacg    9420
caggtatcgt attaattgat ctgcatcaac ttaacgtaaa aacaacttca gacaatacaa    9480
atcagcgaca ctgaatacgg ggcaacctca tgtcccccccc cccccccccc ctgcaggcat    9540
cgtggtgtca cgctcgtcgt ttggtatggc ttcattcagc tccggttccc aacgatcaag    9600
gcgagttaca tgatccccca tgttgtgcaa aaagcggtt agctccttcg gtcctccgat    9660
cgttgtcaga agtaagttgg ccgcagtgtt atcactcatg gttatggcag cactgcataa    9720
ttctcttact gtcatgccat ccgtaagatg cttttctgtg actggtgagt actcaaccaa    9780
gtcattctga gaatagtgta tgcggcgacc gagttgctct tgcccggcgt caacacggga    9840
taataccgcg ccacatagca gaactttaaa agtgctcatc attggaaaac gttcttcggg    9900
gcgaaaactc tcaaggatct taccgctgtt gagatccagt tcgatgtaac ccactcgtgc    9960
acccaactga tcttcagcat cttttacttt caccagcgtt tctgggtgag caaaaacagg    10020
aaggcaaaat gccgcaaaaa agggaataag ggcgacacgg aaatgttgaa tactcatact    10080 cttcctttt caatattatt gaagcattta tcagggttat tgtctcatga gcggatacat    10140
atttgaatgt atttagaaaa ataaacaaat aggggttccg cgcacatttc cccgaaaagt    10200
gccacctgac gtctaagaaa ccattattat catgacatta acctataaaa ataggcgtat    10260
cacgaggccc tttcgtcttc aagaattggt cgacgatctt gctgcgttcg gatattttcg    10320
tggagttccc gccacagacc cggattgaag gcgagatcca gcaactcgcg ccagatcatc    10380
ctgtgacgga actttggcgc gtgatgactg gccaggacgt cggccgaaag agcgacaagc    10440
agatcacgct tttcgacagc gtcggatttg cgatcgagga tttttcggcg ctgcgctacg    10500
tccgcgaccg cgttgaggga tcaagccaca gcagcccact cgaccttcta gccgacccag    10560
acgagccaag ggatcttttt ggaatgctgc tccgtcgtca ggctttccga cgtttgggtg    10620
gttgaacaga agtcattatc gcacggaatg ccaagcactc ccgagggaa ccctgtggtt    10680 ggcatgcaca tacaaatgga cgaacggata aaccttttca cgccctttta aatatccgat    10740
tattctaata aacgctcttt tctcttag                                      10768
```

<210> SEQ ID NO 10
<211> LENGTH: 9942
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 10

| | | | | | |
|---|---|---|---|---|---|
| gtttacccgc | caatatatcc | tgtcaaacac | tgatagttta | aactgaaggc | gggaaacgac | 60 |
| aatctgatca | tgagcggaga | attaagggag | tcacgttatg | accccgccg | atgacgcggg | 120 |
| acaagccgtt | ttacgtttgg | aactgacaga | accgcaacgt | tgaaggagcc | actcagccca | 180 |
| agctacctag | gacgcgtaac | cggtctagaa | agcttatgcg | gtgtgaaata | ccgcacagat | 240 |
| gcgtaaggag | aaaataccgc | atcaggcgcc | attcgccatt | caggctgcgc | aactgttggg | 300 |
| aagggcgatc | ggtgcgggcc | tcttcgctat | tacgccagct | ggcgaaaggg | ggatgtgctg | 360 |
| caaggcgatt | aagttgggta | acgccagggt | tttcccagtc | acgacgttgt | aaaacgacgg | 420 |
| ccagtgccaa | gctcagatcc | tagctttaca | tcaaattgaa | taaagaacga | cagttcaaca | 480 |
| tatactccat | ccacactagt | ttattacgtg | tcctagcttt | tccctaaatt | agtttcccta | 540 |
| aatttacata | attcttagaa | attgtatcca | tattttgaag | atcaaatttc | ttccaatgag | 600 |
| ttatttatga | catatatatt | ggtattgcat | tttagtcatc | aaaatatatt | tagaactcta | 660 |
| acaaagctat | acatgattgc | ttaaagacaa | tacccgaaga | aaattgtaat | caagaatact | 720 |
| ctagatgtgt | gccaattgcc | acgtttacat | aaaatcattc | taactttgtt | catcctatgt | 780 |
| ttgtgcattc | atctatgcat | ttaggattac | aattagtctc | aatcttgtag | taattttttca | 840 |
| ttcatagttt | gatcagttct | cgtctatcta | ctatgcttgt | tcaaccacga | gaagaatatt | 900 |
| agacaatatc | catttataaa | cgctttgata | gcaaacttta | catattcatc | atgtcggtaa | 960 |
| aatggaacat | ttatgatgtg | gttaaggttg | tcgcatgtgt | aaaggtgaag | agatgatgca | 1020 |
| tgtcatccaa | gtatatgaaa | agaattccta | tagaaaatga | caattttttct | tgtaggtaat | 1080 |
| ggaaactagc | tttccagcaa | agaccatata | atctgatgaa | actgataacc | aaatgtcgaa | 1140 |
| attgagtagg | tgccatatca | ttgatagctt | atctattgtt | tggcaaaaag | ataaaatcca | 1200 |
| aatatatata | tatgagatct | cacctatata | aatatctccc | aaatcagtag | ttaatccatc | 1260 |
| gcccataata | ttttgagcat | tcaaaaacac | acaaagggaa | gtgcatcgac | ggatcaagtg | 1320 |
| caaaggtccg | ccttgtttct | cctctgtctc | ttgatctgac | taatcttggt | ttatgattcg | 1380 |
| ttgagtaatt | ttggggaaag | cttcgtccac | agttttttttt | tcgatgaaca | gtgccgcagt | 1440 |
| ggcgctgatc | ttgtatgcta | tcctgcaatc | gtggtgaact | tatgtctttt | atatccttca | 1500 |
| ctaccatgaa | aagactagta | atctttctcg | atgtaacatc | gtccagcact | gctattaccg | 1560 |
| tgtggtccat | ccgacagtct | ggctgaacac | atcatacgat | attgagcaaa | gatcgatcta | 1620 |
| tcttccctgt | tctttaatga | aagacgtcat | tttcatcagt | atgatctaag | aatgttgcaa | 1680 |
| cttgcaagga | ggcgtttctt | tctttgaatt | taactaactc | gttgagtggc | cctgtttctc | 1740 |
| ggacgtaagg | cctttgctgc | tccacacatg | tccattcgaa | ttttaccgtg | tttagcaagg | 1800 |
| gcgaaaagtt | tgcatcttga | tgatttagct | tgactatgcg | attgctttcc | tggacccgtg | 1860 |
| cagctgcgga | cggatccacc | atggcgaaca | agcacctgag | cctctccctc | ttcctcgtgc | 1920 |
| tcctcggcct | ctccgcctcc | ctcgccgcg | gccgccgga | cttctgcctc | gagccgccat | 1980 |
| acaccggacc | ctgcaaggcc | aggatcatcc | gctacttcta | caacgccaag | gccggcctct | 2040 |

```
gccagacctt cgtttacgga ggctgccgcg ccaagcgcaa caacttcaag agcgctgagg    2100
actgcatgcg cacctgcgga ggcgcctgat aagttaacct agacttgtcc atcttctgga    2160
ttggccaact taattaatgt atgaaataaa aggatgcaca catagtgaca tgctaatcac    2220
tataatgtgg gcatcaaagt tgtgtgttat gtgtaattac tagttatctg aataaaagag    2280
aaagagatca tccatatttc ttatcctaaa tgaatgtcac gtgtctttat aattctttga    2340
tgaaccagat gcatttcatt aaccaaatcc atatacatat aaatattaat catatataat    2400
taatatcaat tgggttagca aaacaaatct agtctaggtg tgttttgcga atgcggccgc    2460
gctagcggcg cgcccaccgg tgtctagagg ggccgcggac cgaattccca tggagtcaaa    2520
gattcaaata gaggacctaa cagaactcgc cgtaaagact ggcgaacagt tcatacagag    2580
tctcttacga ctcaatgaca agaagaaaat cttcgtcaac atggtggagc acgacacgct    2640
tgtctactcc aaaaatatca agatacagt ctcagaagac caaagggcaa ttgagacttt    2700
tcaacaaagg gtaatatccg gaaacctcct cggattccat tgcccagcta tctgtcactt    2760
tattgtgaag atagtggaaa aggaaggtgg ctcctacaaa tgccatcatt gcgataaagg    2820
aaaggccatc gttgaagatg cctctgccga cagtggtccc aaagatggac ccccacccac    2880
gaggagcatc gtggaaaaag aagacgttcc aaccacgtct tcaaagcaag tggattgatg    2940
tgatatctcc actgacgtaa gggatgacgc acaatcccac tatccttcgc aagacccttc    3000
ctctatataa ggaagttcat ttcatttgga gaggacaggg tacccgggga tccacacgac    3060
accatgtccc ccgagcgccg ccccgtcgag atccgcccgg ccaccgccgc cgacatggcc    3120
gccgtgtgcg acatcgtgaa ccactacatc gagacctcca ccgtgaactt ccgcaccgag    3180
ccgcagaccc gcaggagtg gatcgacgac ctggagcgcc tccaggaccg ctacccgtgg    3240
ctcgtggccg aggtggaggg cgtggtggcc ggcatcgcct acgccggccc gtggaaggcc    3300
cgcaacgcct acgactggac cgtggagtcc accgtgtacg tgtcccaccg ccaccagcgc    3360
ctcggcctcg gctccaccct ctacacccac ctcctcaaga gcatggaggc cagggcttc    3420 aagtccgtgg tggccgtgat cggcctcccg aacgaccgt ccgtgcgcct ccacgaggcc    3480
ctcggctaca ccgcccgcgg cacccgccg gccgccggct acaagcacgg cggctggcac    3540
gacgtcggct tctggcagcg cgacttcgag ctgccggccc cgccgcgccc ggtgcgcccg    3600
gtgacgcaga tctgagtcga cctgcaggca tgccgctgaa atcaccagtc tctctctaca    3660
aatctatctc tctctataat aatgtgtgag tagttcccag ataagggaat tagggttctt    3720
atagggtttc gctcatgtgt tgagcatata agaaacccct tagtatgtatt tgtatttgta    3780 aaatacttct atcaataaaa tttctaattc ctaaaaccaa aatccagtgg cgagctcgaa    3840
ttcagtacat taaaaacgtc cgcaatgtgt tattaagttg tctaagcgtc aatttgttta    3900
caccacaata tatcctgcca ccagccagcc aacagctccc cgaccggcag ctcggcacaa    3960
aatcaccact cgatacaggc agcccatcag tccgggacgg cgtcagcggg agagccgttg    4020
taaggcggca gactttgctc atgttaccga tgctattcgg aagaacggca actaagctgc    4080
cgggtttgaa acacggatga tctcgcggag ggtagcatgt tgattgtaac gatgacagag    4140
cgttgctgcc tgtgatcaaa tatcatctcc ctcgcagaga tccgaattat cagccttctt    4200
attcatttct cgcttaaccg tgacaggctg tcgatcttga gaactatgcc gacataatag    4260
gaaatcgctg gataaagccg ctgaggaagc tgagtggcgc tatttcttta gaagtgaacg    4320
ttgacgatcg tcgaccgtac cccgatgaat taattcggac gtacgttctg aacacagctg    4380
gatacttact tgggcgattg tcatacatga catcaacaat gtacccgttt gtgtaaccgt    4440
```

```
ctcttggagg ttcgtatgac actagtggtt cccctcagct tgcgactaga tgttgaggcc    4500
taacatttta ttagagagca ggctagttgc ttagatacat gatcttcagg ccgttatctg    4560
tcagggcaag cgaaaattgg ccatttatga cgaccaatgc cccgcagaag ctcccatctt    4620
tgccgccata gacgccgcgc ccccttttg gggtgtagaa catccttttg ccagatgtgg     4680
aaaagaagtt cgttgtccca ttgttggcaa tgacgtagta gccggcgaaa gtgcgagacc    4740
catttgcgct atatataagc ctacgatttc cgttgcgact attgtcgtaa ttggatgaac    4800
tattatcgta gttgctctca gagttgtcgt aatttgatgg actattgtcg taattgctta    4860
tggagttgtc gtagttgctt ggagaaatgt cgtagttgga tggggagtag tcatagggaa    4920
gacgagcttc atccactaaa acaattggca ggtcagcaag tgcctgcccc gatgccatcg    4980
caagtacgag gcttagaacc accttcaaca gatcgcgcat agtcttcccc agctctctaa    5040
cgcttgagtt aagccgcgcc gcgaagcggc gtcggcttga acgaattgtt agacattatt    5100
tgccgactac cttggtgatc tcgcctttca cgtagtgaac aaattcttcc aactgatctg    5160
cgcgcgaggc caagcgatct tcttgtccaa gataagcctg cctagcttca agtatgacgg    5220
gctgatactg ggccggcagg cgctccattg cccagtcggc agcgacatcc ttcggcgcga    5280
ttttgccggt tactgcgctg taccaaatgc gggacaacgt aagcactaca tttcgctcat    5340
cgccagccca gtcgggcggc gagttccata gcgttaaggt ttcatttagc gcctcaaata    5400
gatcctgttc aggaaccgga tcaaagagtt cctccgccgc tggacctacc aaggcaacgc    5460
tatgttctct tgcttttgtc agcaagatag ccagatcaat gtcgatcgtg gctggctcga    5520
agatacctgc aagaatgtca ttgcgctgcc attctccaaa ttgcagttcg cgcttagctg    5580
gataacgcca cggaatgatg tcgtcgtgca caacaatggt gacttctaca gcgcggagaa    5640
tctcgctctc tccaggggaa gccgaagttt ccaaaaggtc gttgatcaaa gctcgccgcg    5700
ttgtttcatc aagccttacg gtcaccgtaa ccagcaaatc aatatcactg tgtggcttca    5760
ggccgccatc cactgcggag ccgtacaaat gtacggccag caacgtcggt tcgagatggc    5820
gctcgatgac gccaactacc tctgatagtt gagtcgatac ttcggcgatc accgcttccc    5880
tcatgatgtt taactcctga attaagccgc gccgcgaagc ggtgtcggct tgaatgaatt    5940
gttaggcgtc atcctgtgct cccgagaacc agtaccagta catcgctgtt tcgttcgaga    6000
cttgaggtct agttttatac gtgaacaggt caatgccgcc gagagtaaag ccacattttg    6060
cgtacaaatt gcaggcaggt acattgttcg tttgtgtctc taatcgtatg ccaaggagct    6120
gtctgcttag tgcccacttt ttcgcaaatt cgatgagact gtgcgcgact cctttgcctc    6180
ggtgcgtgtg cgacacaaca atgtgttcga tagaggctag atcgttccat gttgagttga    6240
gttcaatctt cccgacaagc tcttggtcga tgaatgcgcc atagcaagca gagtcttcat    6300
cagagtcatc atccgagatg taatccttcc ggtagggggct cacacttctg gtagatagtt    6360
caaagccttg gtcggatagg tgcacatcga acacttcacg aacaatgaaa tggttctcag    6420
catccaatgt ttccgccacc tgctcaggga tcaccgaaat cttcatatga cgcctaacgc    6480
ctggcacagc ggatcgcaaa cctgcgcgcg cttttggcac aaaaggcgtg acaggtttgc    6540
gaatccgttc ctgccacttg ttaacccttt tgccagattt ggtaactata atttatgtta    6600
gaggcgaagt cttgggtaaa aactggccta aaattgctgg ggatttcagg aaagtaaaca    6660
tcaccttccg gctcgatgtc tattgtagat atatgtagtg tatctacttg atcggggat    6720 ctgctgcctc gcgcgtttcg gtgatgacgg tgaaaacctc tgcacacatgc agctcccgga   6780
```

```
gacggtcaca gcttgtctgt aagcggatgc cgggagcaga caagcccgtc agggcgcgtc    6840
agcgggtgtt ggcgggtgtc ggggcgcagc catgacccag tcacgtagcg atagcggagt    6900
gtatactggc ttaactatgc ggcatcagag cagattgtac tgagagtgca ccatatgcgg    6960
tgtgaaatac cgcacagatg cgtaaggaga aataccgca tcaggcgctc ttccgcttcc     7020
tcgctcactg actcgctgcg ctcggtcgtt cggctgcggc gagcggtatc agctcactca    7080
aaggcggtaa tacggttatc cacagaatca ggggataacg caggaaagaa catgtgagca    7140
aaaggccagc aaaaggccag gaaccgtaaa aaggccgcgt tgctggcgtt tttccatagg    7200
ctccgccccc ctgacgagca tcacaaaaat cgacgctcaa gtcagaggtg gcgaaacccg    7260
acaggactat aaagatacca ggcgtttccc cctggaagct ccctcgtgcg ctctcctgtt    7320
ccgaccctgc cgcttaccgg atacctgtcc gcctttctcc cttcgggaag cgtggcgctt    7380
tctcatagct cacgctgtag gtatctcagt tcggtgtagg tcgttcgctc caagctgggc    7440
tgtgtgcacg aacccccccgt tcagcccgac cgctgcgcct tatccggtaa ctatcgtctt    7500
gagtccaacc cggtaagaca cgacttatcg ccactggcag cagccactgg taacaggatt    7560
agcagagcga ggtatgtagg cggtgctaca gagttcttga agtggtggcc taactacggc    7620
tacactagaa ggacagtatt tggtatctgc gctctgctga gccagttac cttcggaaaa    7680
agagttggta gctcttgatc cggcaaacaa accaccgctg gtagcggtgg tttttttgtt    7740
tgcaagcagc agattacgcg cagaaaaaaa ggatctcaag aagatccttt gatcttttct    7800
acggggtctg acgctcagtg gaacgaaaac tcacgttaag ggattttggt catgagatta    7860
tcaaaaagga tcttcaccta gatccttta aattaaaaat gaagttttaa atcaatctaa    7920
agtatatatg agtaaacttg gtctgacagt taccaatgct taatcagtga ggcacctatc    7980
tcagcgatct gtctatttcg ttcatccata gttgcctgac tccccgtcgt gtagataact    8040
acgatacggg agggcttacc atctggcccc agtgctgcaa tgataccgcg agacccacgc    8100
tcaccggctc cagatttatc agcaataaac cagccagccg aagggccga gcgcagaagt    8160
ggtcctgcaa cttttatccgc ctccatccag tctattaatt gttgccggga agctagagta    8220
agtagttcgc cagttaatag tttgcgcaac gttgttgcca ttgctgcagg ggggggggg    8280
gggggggact tccattgttc attccacgga caaaaacaga gaaggaaac gacagaggcc    8340
aaaaagcctc gctttcagca cctgtcgttt cctttctttt cagagggtat tttaaataaa    8400
aacattaagt tatgacgaag aagaacggaa acgccttaaa ccggaaaatt ttcataaata    8460
gcgaaacccc gcgaggtcgc cgccccgtaa cctgtcggat caccgaaaag gacccgtaaa    8520
gtgataatga ttatcatcta catatcacaa cgtgcgtgga ggccatcaaa ccacgtcaaa    8580
taatcaatta tgacgcaggt atcgtattaa ttgatctgca tcaacttaac gtaaaaacaa    8640
cttcagacaa tacaaatcag cgacactgaa tacggggcaa cctcatgtcc ccccccccc    8700
ccccccctgca ggcatcgtgg tgtcacgctc gtcgtttggt atggcttcat tcagctccgg    8760
ttcccaacga tcaaggcgag ttacatgatc ccccatgttg tgcaaaaaag cggttagctc    8820
cttcggtcct ccgatcgttg tcagaagtaa gttggccgca gtgttatcac tcatggttat    8880
ggcagcactg cataattctc ttactgtcat gccatccgta agatgctttt ctgtgactgg    8940
tgagtactca accaagtcat tctgagaata gtgtatgcgg cgaccgagtt gctcttgccc    9000
ggcgtcaaca cggaataata ccgcgccaca tagcagaact ttaaaagtgc tcatcattgg    9060
aaaacgttct tcggggcgaa aactctcaag gatcttaccg ctgttgagat ccagttcgat    9120
gtaacccact cgtgcaccca actgatcttc agcatctttt actttcacca gcgtttctgg    9180
```

```
gtgagcaaaa acaggaaggc aaaatgccgc aaaaaaggga ataagggcga cacggaaatg    9240
ttgaatactc atactcttcc tttttcaata ttattgaagc atttatcagg gttattgtct    9300
catgagcgga tacatatttg aatgtattta gaaaaataaa caaataggga ttccgcgcac    9360
atttccccga aaagtgccac ctgacgtcta agaaaccatt attatcatga cattaaccta    9420
taaaaatagg cgtatcacga ggccctttcg tcttcaagaa ttggtcgacg atcttgctgc    9480
gttcggatat tttcgtggag ttcccgccac agacccggat tgaaggcgag atccagcaac    9540
tcgcgccaga tcatcctgtg acggaacttt ggcgcgtgat gactggccag gacgtcggcc    9600
gaaagagcga caagcagatc acgcttttcg acagcgtcgg atttgcgatc gaggattttt    9660
cggcgctgcg ctacgtccgc gaccgcgttg agggatcaag ccacagcagc ccactcgacc    9720
ttctagccga cccagacgag ccaagggatc tttttggaat gctgctccgt cgtcaggctt    9780
tccgacgttt gggtggttga acagaagtca ttatcgtacg gaatgccaag cactcccgag    9840
gggaaccctg tggttggcat gcacataaa atggacgaac ggataaacct tttcacgccc     9900
ttttaaatat ccgttattct aataaacgct cttttctctt ag                       9942
```

<210> SEQ ID NO 11  
<211> LENGTH: 4  
<212> TYPE: PRT  
<213> ORGANISM: Unknown  
<220> FEATURE:  
<223> OTHER INFORMATION: Description of Unknown: "KDEL" family motif peptide

<400> SEQUENCE: 11

Lys Asp Glu Leu  
1

<210> SEQ ID NO 12  
<211> LENGTH: 13  
<212> TYPE: DNA  
<213> ORGANISM: Unknown  
<220> FEATURE:  
<223> OTHER INFORMATION: Description of Unknown: Kozak consensus sequence

<400> SEQUENCE: 12
gccgccrcca tgg                                                       13

PERICARP TISSUE PREFERRED REGULATORY REGION AND METHOD OF USING SAME

REFERENCE TO RELATED APPLICATION

This application claims priority to previously filed application U.S. Ser. No. 61/644,333, filed May 8, 2012, the contents of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Mar. 7, 2013, is named AB00013_SL.txt and is 36,323 bytes in size.

BACKGROUND OF THE INVENTION

Promoters are vital molecular tools that have been applied widely in plant biotechnology to control the expression of introduced genes. There are many applications for promoters in driving gene expression in plant tissues. These include the synthesis of scoreable and selectable markers to identify transgenic plants (Jefferson et al., 1987; Wohlleben et al., 1988) and the over-expression of control point enzymes to modify metabolic flux through key pathways, so affecting the yields of important plant products (Nessler, 1994; Lessard et al., 2002). Other uses of plant promoters include the expression of genes conferring resistance to pests, thus conferring protection (Estruch et al., 1997), and the expression of non-native enzymes to facilitate the production of foreign metabolites in particular plant species (Poirier et al., 1995; Ye et al., 2000). A further application of plant promoters is to over-express controlling regulatory genes affecting aspects of plant physiology such as flowering time and so modify plant growth characteristics (Weigel and Nilsson, 1995). Promoters are also used to repress the expression of specific genes by driving the synthesis of interfering RNA species (Waterhouse et al., 2001), thus affecting plant metabolic and developmental pathways (Yu and Kumar, 2003). Although high levels of expression may not be necessary for all of the above applications, there is clearly a need for promoters showing activity in specific plant tissues.

Apart from these and other applications of promoters to modify plant traits, promoters are also required for plants to act as production systems for heterologous proteins. Plants have been used to produce a wide range of recombinant proteins of potential economic and/or medicinal importance. These include research chemicals (Hood et al., 1997; Zhong et al., 1999), processing enzymes that are used, for example, in the pharmaceutical industry (Woodard et al., 2003), industrial enzymes that are deployed in large-scale processing operations such as bleaching (Hood et al., 2003; Bailey et al., 2004), candidate vaccine antigens for animal or plant disease prevention (Mason et al., 1992; Haq et al., 1995; Carrillo et al., 1998; Streatfield et al., 2001), and therapeutic pharmaceuticals including antibodies (Daniell et al., 2001; Hood et al., 2002). The expressed proteins may either be purified from the plant tissues (Hood et al., 1997; Woodard et al., 2003) or, if as with vaccines the final application allows it, the recombinant plant material may be processed into a suitable form for use or even deployed directly (Streatfield et al., 2002; Lamphear et al., 2002). For these and other protein products to be produced in plant systems it is necessary that promoters drive a sufficiently high level of expression to ensure commercial viability.

Spatial and temporal control is also often important in driving gene expression in plants. For example, selectable and scoreable markers must be expressed at a suitable time and in an appropriate tissue to allow for screening, and controlling enzymes and regulatory factors must be produced in metabolically active and physiologically responsive tissues, respectively. Similarly, genes conferring host protection must be expressed in the target tissues for the pathogen or pest, and plant produced protein products should be expressed in tissues suitable for protein accumulation and storage. Furthermore, since certain protein products may have detrimental affects on plant health and yield when expressed in metabolically active plant tissues that are essential for survival and growth, promoters may be favored that are active in the chosen plant storage tissues but show low or no activity in other, non-storage tissues.

Promoters that preferentially express relatively high levels of foreign proteins in tissues suitable for stable protein accumulation and storage are particularly useful for commercial protein production. The seed tissues of the cereals are especially well suited to the large-scale production of recombinant proteins. Thus, there is a requirement for promoters that show a seed tissue preferred expression pattern in plants and particularly cereals and drive relatively high levels of protein accumulation in these tissues.

Several promoters of plant and plant pathogen (bacterial and viral) origin have been used to direct transgene expression in plants. Prominent examples include the French bean beta-phaseolin promoter (Bustos et al., 1989), the mannopine synthase promoter of *Agrobacterium tumefaciens* (Leung et al., 1991), and the 35S promoter of cauliflower mosaic virus (Guilley et al., 1982). These and several other promoters in widespread use in plants were originally developed and utilized in dicot species. Promoter sequences from one species are predictably used in other species (see discussion below). The cereals comprise particularly important crops and there is therefore a pressing need for promoters that have high activity and/or tissue preference in monocots. Cereals, such as grasses, are cultivated for their grain. Since the nutritional value of cereals is in their seeds, and these tissues are also well suited for recombinant protein accumulation and storage, promoters that are active in cereal seed tissues are especially useful.

Two broad classes of promoters are typically deployed: constitutive and tissue preferred. Constitutive promoters, such as maize polyubiquitin-1 drive expression in the seed but also in other tissues (Christensen et al., 1992). A drawback with such constitutive promoters is that expression in tissues other than seed storage tissues may result in plant health being compromised, for example if a potentially toxic protein is expressed in metabolically active tissues required for germination or growth (Hood et al., 2003). Furthermore, constitutive expression may result in the expressed foreign protein being synthesized in pollen grains and thus being difficult to contain. By contrast, seed preferred promoters limit all or the bulk of transgene expression to seed tissues, so avoiding such concerns. Tissue preferred expression can include seed preferred expression. An example of one such promoter providing seed preferred expression is the phaseolin promoter. See, Bustos et al. "Regulation of β-glucuronidase Expression in Transgenic Tobacco Plants by an A/T-Rich cis-Acting Sequence Found Upstream of a French Bean β-Phaseolin Gene" *The Plant Cell* Vol. 1, 839-853 (1989).

The principle tissue types in angiosperm seeds are the embryo, the endosperm including a surrounding aleurone cell layer and the maternally derived pericarp. The pericarp is the mature ovary wall and encloses the seeds. Preferentially directing expression of a nucleic acid molecule to the pericarp tissue is advantageous in a number of different applications.

All references cited herein are incorporated herein by reference.

SUMMARY OF THE INVENTION

A regulatory from a gene of *Zea mays* has been identified and has preferential expression to the pericarp of a plant seed. In an embodiment, it is used to drive expression in plants, in an embodiment driving expression in pericarp in angiosperm plant seed plants, particularly cereal plants, and in a further embodiment, in maize.

DESCRIPTION OF THE DRAWINGS

FIG. 1 shows the nucleotide sequence of the promoter with the minimal promoter in bold (SEQ ID NO: 1), the TATA box underlined, the putative leader sequence in italics (SEQ ID NO: 5) and the ATG start in capital letters. The entire promoter, leader sequence and ATG start site is SEQ ID NO: 3.

DESCRIPTION OF THE PREFERRED EMBODIMENTS

Figure 2:
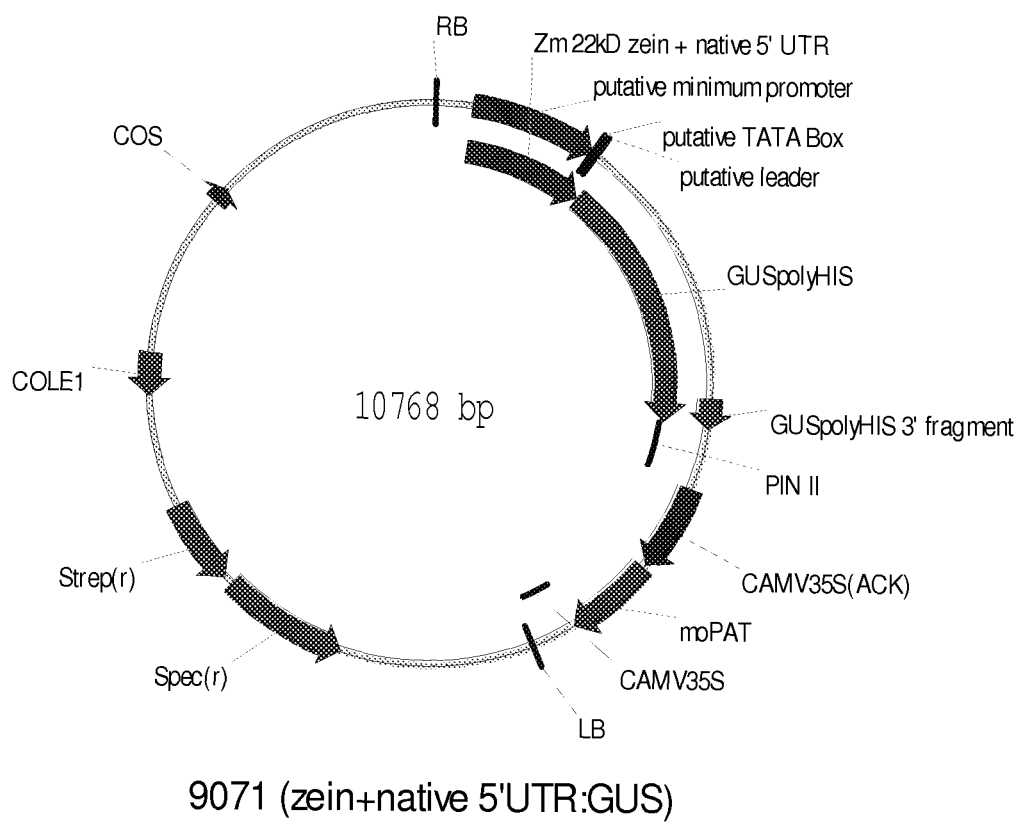
FIG. 2 is a diagram showing a vector map of a construct 9071 with the zein pericarp promoter using the entire promoter including the 5' leader and including the ATG site fused to GUS with a pinII terminator in a vector designed for *Agrobacterium* transformation with a left border (LB) and right border (RB) of *Agrobacterium*, the 35S promoter driving the maize optimized phosphinothricin marker gene (moPAT) and 35S terminator and bacterial genes for *Agrobacterium* selection

Nucleotide sequences are described herein that regulate transcription with preferential expression to plant seed tissue, and preferential expression to plant pericarp tissue in the seed. These novel nucleotide sequences are to a *Zea mays* pericarp-preferred regulatory region designated also as PR3.

A genomics approach can be used and is described to identify further sequences that can drive high levels of transgene expression in pericarp tissues. The maize zein genes are a subset of the prolamin storage proteins. Twenty-three gene family members have been identified for the maize 22 kd α-zein protein in the BSSS53 inbred (Song, et al (2001) *Genome Res* 11:1817-1825, Song, et al. (2003) *Proc Natl Acad Sci USA* 100 (15):9055-9060. Twenty-two of these are clustered closely together on chromosome 4 and one unlinked gene, further from the others on chromosome 4, corresponds to the floury-2 locus. The expression of these genes has been reported to be largely restricted to the endosperm (Locatelli, et al (2009) *Plant Cell* 21 (5):1410-1427, Feng (2009) *Plant Mol Biol* 69 (6):649-659, Miclaus, (2011) *PLoS Genet.* 7 (6):e1002131. Shown here is a promoter from the maize 22 kd zein gene family that drives gene expression preferentially in the pericarp. The promoter sequence is shown in FIG. 1. The 787 bp promoter is shown in bold and is SEQ ID NO: 1. As one skilled in the art appreciates, the promoter may be combined with the leader sequence of the PR3 promoter, the TATA box of the PR3 promoter, or with the leader sequence and TATA box of another promoter, or combination. The putative leader sequence is in italics (SEQ ID NO: 5) and the ATG start in capital letters. The entire 889 bp promoter, leader sequence and ATG start site is SEQ ID NO: 3. The region in bold upstream of the TATA box marked as the promoter includes the regulatory information necessary for tissue-specific expression. Transgenic plants generated using this sequence show expression in the pericarp and did not express in other portions of the seed. Tissue from root, leaf, stem, cob, and silk tissue was examined and did not show significant staining except in a small portion of tissue at the junction of the cob with the developing kernel. In developing seeds, staining was not detected at twelve days after pollination but was observed in the pericarp at 19 days after pollination.

Thus, this new pericarp preferred promoter PR3 is well suited to drive transgene expression in pericarp of plant seeds. As is evident to one skilled in the art, the promoter may be used with any convenient heterologous nucleic acid molecule, which can be from a source foreign to the cell, or where endogenous may be a molecule not naturally found next to the adjacent molecule, may be introduced into the cell by human intervention, or may be or modified from its original composition. There are many applications for a pericarp preferred promoter, as, for example, use with a color reporter gene that can identify presence of the reporter, and any linked gene, by changing color of the pericarp of the seed; by expressing a gene of interest to that tissue, such as those impacting pericarp composition or providing, for example, disease or stress resistance or other desired agronomic impact; or directing expression of an interfering sequence to the pericarp; or expressing industrial, pharmaceutical or other proteins to the pericarp. Impacting the pericarp composition can, for example, change the chemical, physical, nucleic acids, amino acids or other molecular characteristics of the pericarp tissue. The pericarp tissue may be impacted by changing one or more chemical, physical, nucleic acids, amino acids or other molecular characteristics of the pericarp tissue compared to pericarp tissue which does not comprise the regulatory region operably linked to the nucleic acid molecule impacting the tissue.

By way of example without limitation, the heterologous nucleic acid molecule may be one which provides a visually observable color change, thus allowing for easy identification of seeds expressing the construct comprising the pericarp preferred promoter and operably linked nucleic acid molecule. In another example, the composition of the pericarp itself may be impacted. It has been noted there is a correlation between pericarp thickness and disease susceptibility to *Fusarium* ear rot. Hoenisch and Davis (1994) *Plant disease* 78: 517-519 The ability to store seed for long periods can be improved by changing pericarp composition. In still further examples, thinner pericarp may be desired where the seed, as corn, is used in the fresh corn industry, or for producing popcorn. Ito and Brewbaker (1991) *Journal of* the *American Society for Horticultural Science* 116: 1072-1177; Tandjung et al. (2005) *Biomacromolecules* 6: 1654-1660.

One skilled in the art will appreciate that there are a vast variety of uses of such a promoter. The promoter of the invention may be usefully employed with any nucleic acid molecule, and is particularly advantageous where preferred expression to the pericarp tissue of a plant is preferred.

In addition to being used to drive a protein-producing nucleic acid molecule, the promoter of the invention can be used with any nucleic acid molecule whether it produces protein or not. The promoter can be used to drive mRNA that can be used for any such silencing system, such as antisense, where no protein is produced. Nellen et al. (1993) *TIBS* 18:419-423; Alexander et al. (1988) *Gene* 72:45-50. Means of increasing or inhibiting a protein are well known to one skilled in the art and, by way of example, may include, beside antisense suppression, transgenic expression, use of hairpin formations, co-suppression methods including but not limited to: RNA interference, gene activation or suppression using transcription factors and/or repressors, mutagenesis including transposon tagging, directed and site-specific mutagenesis, chromosome engineering and, homologous recombination. In the case of use with homologous recombination, no in vivo construct will be required. A few of the myriad of examples of such systems available include use of the Mu transposon, Chandler et al. (1994) *The Maize Handbook* ch. 118 Springer-Verlag; RNA interference (U.S. Pat. No. 5,034,323); use of hairpins, Smith et al. (2000) *Nature* 407:319-320 and ribozymes (Steinecke et al. (1992) *EMBOL J.* 11: 1525; and zinc-finger targeted molecules, WO 01/52620. Clearly many options are available for impacting a targeted protein.

The promoter can be used in any plant species, including, for example, a monocotyledonous plant, including but not limited to wheat, rye, rice, oat, barley, turfgrass, sorghum, millet or sugarcane. Alternatively, the plant may be a dicotyledonous plant, including but not limited to tobacco, tomato, potato, soybean, cotton, canola, sunflower or alfalfa. Maize promoters have been used repeatedly to drive expression of genes in non-maize plants, including tobacco (Yang and Russell (1990) "Maize sucrose synthase-1 promoter drives phloem cell-specific expression of GUS gene in transgenic tobacco plants" *Proc. Natl. Acad. Sci. USA* 87, 4144-4148; Geffers et al., (2000) "Anaerobiosis-specific interaction of tobacco nuclear factors with cis-regulatory sequences in the maize GapC4 promoter" *Plant Mol. Biol.* 43, 11-21; Vilardell et al., (1991) "Regulation of the maize rab 17 gene promoter in transgenic heterologous systems" *Plant Mol. Biol.* 17, 985-993), cultured rice cells (Vilardell et al. (1991), supra), wheat (Oldach et al., (2001) "Heterologous expression of genes mediating enhanced fungal resistance in transgenic wheat" *Mol. Plant. Microbe Interact.* 14, 832-838; Brinch-Pedersen et al., (2003) "Concerted action of endogenous and heterologous phytase on phytic acid degradation in seed of transgenic wheat (*Triticum aestivum* L.)" *Transgenic Res.* 12, 649-659), rice (Cornejo et al., (1993) "Activity of a maize ubiquitin promoter in transgenic rice" *Plant Mol. Biol.* 23, 567-581; Takimoto et al., (1994) "Non-systemic expression of a stress-response maize polyubiquitin gene (Ubi-1) in transgenic rice plants" *Plant Mol. Biol.* 26, 1007-1012), sunflower (Roussell et al., (1988) "Deletion of DNA sequences flanking an Mr 19,000 zein gene reduces its transcriptional activity in heterologous plant tissues" *Mol. Gen. Genet.* 211, 202-209) and protoplasts of carrot (Roussell et al., 1988, supra).

The nucleotide sequences of the invention can be used to isolate corresponding sequences from other organisms, particularly other plants, or to synthesize synthetic sequences. In this manner, methods such as PCR, hybridization, synthetic gene construction and the like can be used to identify or generate such sequences based on their sequence homology to the sequences set forth herein. Sequences identified, isolated or constructed based on their sequence identity to the whole of or any portion of the zein pericarp promoter set forth herein are encompassed by the present invention. In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed (Sambrook et al., 1989; Innis et al., 1990; Innis et al., 1995; Innis et al., 1999). Known methods of PCR include, but are not limited to, methods using paired primers, nested primers, degenerate primers, gene-specific primers, vector-specific primers, partially-mismatched primers, and the like. Once isolated, many methods are available for one skilled in the art to detect pericarp-preferred expression. Any method by which one can confirm the promoter drives transcription in a pericarp-preferred manner can be used to detect pericarp-preferred transcription. An example of one such method is operably linking the isolated regulatory region to a scoreable marker, and observing expression in various plant tissues. Examples of a number of such screenable or scoreable markers are described below.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledons or dicotyledons as these preferences have been shown to differ (Murray et al. *Nucl. Acids Res.* 17:477-498 (1989)). Thus, the maize preferred codon for a particular amino acid may be derived from known gene sequences from maize. Maize codon usage for 28 genes from maize plants are listed in Table 4 of Murray et al., supra.

With reference to nucleic acid molecules, the term isolated nucleic acid is sometimes used. This term, when applied to DNA, refers to a DNA molecule that is separated from sequences with which it is immediately contiguous (in the 5' and 3' directions) in the naturally occurring genome of the organism from which it was derived. For example, the isolated nucleic acid may comprise a DNA molecule inserted into a vector, such as a plasmid or virus vector, or integrated into the genomic DNA of a prokaryote or eukaryote. An isolated nucleic acid molecule may also comprise a cDNA molecule.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the DNA sequences of the invention. Methods for preparation of probes for hybridization and for construction of cDNA and genomic libraries are generally known in the art and are disclosed (Sambrook et al., 1989).

For example, the pericarp promoter disclosed herein, or one or more portions thereof, may be used as a probe capable of specifically hybridizing to corresponding sequences. To achieve specific hybridization under a variety of conditions, such probes include sequences that are unique among the sequences to be screened and are preferably at least about 10 nucleotides in length, and most preferably at least about 20 nucleotides in length. Such sequences may alternatively be used to amplify corresponding sequences from a chosen plant by PCR. This technique may be used to isolate sequences from a desired plant or as a diagnostic assay to determine the presence of sequences in a plant. Hybridization techniques include hybridization screening of DNA libraries plated as either plaques or colonies (Sambrook et al., 1989).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20.times.SSC=3.0 M NaCl/0.3 M trisodium citrate) at 50 to 55° C. Exemplary moderate stringency conditions include hybridization in 40 to 45% formamide, 1.0 M NaCl, 1% SDS at 37.degree. C., and a wash in 0.5× to 1×SSC at 55 to 60.degree. C. Exemplary high stringency conditions include hybridization in 50% formamide, 1.0 M NaCl, 1% SDS at 37° C., and a wash in 0.1×SSC at 60 to 65° C.

Specificity is also the function of post-hybridization washes, the critical factors being the ionic strength and temperature of the final wash solution. For DNA-DNA hybrids, the $T_m$ can be approximated from the equation $T_m$=81.5° C.+16.6 (log M)+0.41(% GC)−0.61(% form.)−500/L, where M is the molarity of monovalent cations, % GC is the percentage of guanosine and cytosine nucleotides in the DNA, % form. is the percentage of formamide in the hybridization solution, and L is the length of the hybrid in base pairs (Meinkoth and Wahl, 1984). The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted for sequences of the desired identity to hybridize. For example, if sequences with 90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11 to 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Ausubel et al. (1993) and Sambrook et al. (1989).

Thus, isolated sequences that have promoter activity and which hybridize under stringent conditions to the promoter sequences disclosed herein, or to fragments thereof, are encompassed by the present invention.

The following terms are used to describe the sequence relationships between two or more nucleic acids or polynucleotides: (a) "reference sequence", (b) "comparison window", (c) "sequence identity" and (d) "percentage of sequence identity."

(a) As used herein, "reference sequence" is a defined sequence used as a basis for sequence comparison. A reference sequence may be a subset or the entirety of a specified sequence; for example, as a segment of a full-length promoter sequence, or the complete promoter sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to accurately reflect the similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm.

Optimal alignment of sequences for comparison can use any means to analyze sequence identity (homology) known in the art, e.g., by the progressive alignment method of termed "PILEUP" (Morrison, (1997) *Mol. Biol. Evol.* 14:428-441, as an example of the use of PILEUP); by the local homology algorithm of Smith & Waterman (*Adv. Appl. Math.* 2: 482 (1981)); by the homology alignment algorithm of Needleman & Wunsch (*J. Mol. Biol.* 48:443-453 (1970)); by the search for similarity method of Pearson (*Proc. Natl. Acad. Sci. USA* 85: 2444 (1988)); by computerized implementations of these algorithms (e.g., GAP, BEST FIT, FASTA, and TFASTA in the Wisconsin Genetics Software Package, Genetics Computer Group, 575 Science Dr., Madison, Wis.); ClustalW (CLUSTAL in the PC/Gene program by Intelligenetics, Mountain View, Calif., described by, e.g., Higgins (1988), *Gene* 73: 237-244; Corpet (1988), *Nucleic*

*Acids Res.* 16:10881-10890; Huang, *Computer Applications in the Biosciences* 8:155-165 (1992); and Pearson (1994), *Methods in Mol. Biol.* 24:307-331); Pfam (Sonnhammer (1998), *Nucleic Acids Res.* 26:322-325); TreeAlign (Hein (1994), *Methods Mol. Biol.* 25:349-364); MEG-ALIGN, and SAM sequence alignment computer programs; or, by manual visual inspection.

Another example of algorithm that is suitable for determining sequence similarity is the BLAST algorithm, which is described in Altschul et al, (1990) *J. Mol. Biol.* 215: 403-410. The BLAST programs (Basic Local Alignment Search Tool) of Altschul, S. F., et al., (1993) *J. Mol. Biol.* 215:403-410) searches under default parameters for identity to sequences contained in the BLAST "GENEMBL" database. A sequence can be analyzed for identity to all publicly available DNA sequences contained in the GENEMBL database using the BLASTN algorithm under the default parameters.

Software for performing BLAST analyses is publicly available through the National Center for Biotechnology Information, world wide web ncbi.nlm.nih.gov/; see also Zhang (1997), Genome Res. 7:649-656 for the "Power-BLAST" variation. This algorithm involves first identifying high scoring sequence pairs (HSPs) by identifying short words of length W in the query sequence that either match or satisfy some positive valued threshold score T when aligned with a word of the same length in a database sequence. T is referred to as the neighborhood word score threshold (Altschul et al (1990), J. Mol. Biol. 215: 403-410). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a wordlength (W) of 11, the BLOSUM62 scoring matrix (see Henikoff (1992), Proc. Natl. Acad. Sci. USA 89:10915-10919) alignments (B) of 50, expectation (E) of 10, M=5, N=4, and a comparison of both strands. The term BLAST refers to the BLAST algorithm which performs a statistical analysis of the similarity between two sequences; see, e.g., Karlin (1993), Proc. Natl. Acad. Sci. USA 90:5873-5787. One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

In an embodiment, GAP (Global Alignment Program) can be used. GAP uses the algorithm of Needleman and Wunsch (*J. Mol. Biol.* 48:443-453, 1970) to find the alignment of two complete sequences that maximizes the number of matches and minimizes the number of gaps. Default gap creation penalty values and gap extension penalty values in the commonly used Version 10 of the Wisconsin Package® (Accelrys, Inc., San Diego, Calif.) for protein sequences are 8 and 2, respectively. For nucleotide sequences the default gap creation penalty is 50 while the default gap extension penalty is 3. Percent Similarity is the percent of the symbols that are similar. Symbols that are across from gaps are ignored. A similarity is scored when the scoring matrix value for a pair of symbols is greater than or equal to 0.50, the similarity threshold. A general purpose scoring system is the BLOSUM62 matrix (Henikoff and Henikoff (1993), *Proteins* 17: 49-61), which is currently the default choice for BLAST programs. BLOSUM62 uses a combination of three matrices to cover all contingencies. Altschul, J. Mol. Biol. 36: 290-300 (1993), herein incorporated by reference in its entirety and is the scoring matrix used in Version 10 of the Wisconsin Package® (Accelrys, Inc., San Diego, Calif.) (see Henikoff & Henikoff (1989) *Proc. Natl. Acad. Sci. USA* 89:10915).

(c) As used herein, "sequence identity" or "identity" in the context of two nucleic acid sequences makes reference to the residues in the two sequences that are the same when aligned for maximum correspondence over a specified comparison window.

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison, and multiplying the result by 100 to yield the percentage of sequence identity.

Identity to the sequence of the present invention would mean a polynucleotide sequence having at least 65% sequence identity, more preferably at least 70% sequence identity, more preferably at least 75% sequence identity, more preferably at least 80% identity, more preferably at least 85% 86%, 87%, 88%, 89%, 90%, 91%, 92%, 93%, 94%, 95%, 96%, 97%, 98%, 99% sequence identity.

The invention is further to "functional variants" of the regulatory sequence disclosed. Functional variants include, for example, regulatory sequences of the invention having one or more nucleotide substitutions, deletions or insertions and wherein the variant retains promoter activity, particularly the ability to drive expression preferentially to the pericarp of a plant. Functional variants can be created by any of a number of methods available to one skilled in the art, such as by site-directed mutagenesis, induced mutation, identified as allelic variants, cleaving through use of restriction enzymes, or the like. Activity can likewise be measured by any variety of techniques, including measurement of reporter activity as is described at U.S. Pat. No. 6,844,484, Northern blot analysis, or similar techniques. The '484 patent describes the identification of functional variants of different promoters, incorporated herein by reference in its entirety.

The invention further encompasses a "functional fragment" that is a regulatory fragment formed by one or more deletions from a larger regulatory element. For example, the 5' portion of a promoter up to the TATA box near the transcription start site can be deleted without abolishing promoter activity, as described by Opsahl-Sorteberg, H-G. et al., 2004. Such fragments should retain promoter activity, particularly the ability to drive expression of operably linked nucleotide sequences. Activity can be measured by Northern blot analysis, reporter activity measurements when using transcriptional fusions, and the like. See for example, Sambrook et al. (1989). Functional fragments can be obtained by use of restriction enzymes to cleave the naturally occurring regulatory element nucleotide sequences disclosed herein; by synthesizing a nucleotide sequence from the naturally occurring DNA sequence; or can be obtained through the use of PCR technology. See particularly, Mullis et al. (1987) and Erlich, ed. (1989).

For example, a routine way to remove a part of a DNA sequence is to use an exonuclease in combination with DNA amplification to produce unidirectional nested deletions of double stranded DNA clones. A commercial kit for this purpose is sold under the trade name Exo-Size™ (New England Biolabs, Beverly, Mass.). Briefly, this procedure entails incubating exonuclease III with DNA to progressively remove nucleotides in the 3' to 5' direction at the 5' overhangs, blunt ends or nicks in the DNA template. However, the exonuclease III is unable to remove nucleotides at 3' 4-base overhangs. Timed digest of a clone with this enzyme produces unidirectional nested deletions.

As used herein, the term "cis-element" refers to a cis-acting transcriptional regulatory element that confers an aspect of the overall control of gene expression. A cis-element may function to bind transcription factors, trans-acting protein factors that regulate transcription. Some cis-elements bind more than one transcription factor, and transcription factors may interact with different affinities with more than one cis-element.

The promoters of the present invention desirably contain cis-elements that can confer or modulate gene expression. Cis-elements can be identified by a number of techniques, including deletion analysis, i.e., deleting one or more nucleotides from the 5' end or internal to a promoter; DNA binding protein analysis using DNase I footprinting, methylation interference, electrophoresis mobility-shift assays, in vivo genomic footprinting by ligation-mediated PCR, and other conventional assays; or by DNA sequence similarity analysis with known cis-element motifs by conventional DNA sequence comparison methods. The fine structure of a cis-element can be further studied by mutagenesis (or substitution) of one or more nucleotides or by other conventional methods. Cis-elements can be obtained by chemical synthesis or by isolation from promoters that include such elements, and they can be synthesized with additional flanking nucleotides that contain useful restriction enzyme sites to facilitate subsequent manipulation.

The promoter of the invention may be combined with any number of other components to be introduced into the plant, including combined with a gene of interest or nucleic acid sequence of interest to be expressed in the plant. The "gene of interest" or "nucleic acid sequence of interest" refers to a nucleic acid that may encode a desired polypeptide or protein but also may refer to a nucleic acid that does not constitute an entire gene, and which does not necessarily encode a polypeptide or protein. For example, when used in a homologous recombination process, the promoter may be placed in a construct with a sequence that targets an area of the chromosome in the plant but may not encode a protein. As used herein, the terms nucleic acid of interest or polynucleotide refer to deoxyribonucleotides or ribonucleotides and polymers thereof in either single- or double-stranded form. As such, the terms include RNA and DNA, which can be a gene or a portion thereof, a cDNA, a synthetic polydeoxyribonucleic acid sequence, or the like, and can be single-stranded or double-stranded, as well as a DNA/RNA hybrid. Furthermore, the terms are used herein to include naturally-occurring nucleic acid molecules, which can be isolated from a cell, as well as synthetic molecules, which can be prepared, for example, by methods of chemical synthesis or by enzymatic methods such as by the polymerase chain reaction (PCR). Unless specifically limited, the terms encompass nucleic acids containing known analogues of natural nucleotides that have similar binding properties as the reference nucleic acid and are metabolized in a manner similar to naturally occurring nucleotides. The term nucleic acid is used interchangeably with gene, cDNA, and mRNA encoded by a gene.

Unless otherwise indicated, when referring to a particular nucleic acid sequence that encodes an amino acid which may be linked to the promoter of the invention, it also implicitly encompasses conservatively modified variants thereof (e.g. degenerate codon substitutions) and complementary sequences as well as the sequence explicitly indicated.

The term conservatively modified variants applies to both amino acid and nucleic acid sequences. With respect to particular nucleic acid sequences, conservatively modified variants refers to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are silent variations and represent one species of conservatively modified variation. Every nucleic acid sequence herein that encodes a polypeptide also, by reference to the genetic code, describes every possible silent variation of the nucleic acid. One of ordinary skill will recognize that each codon in a nucleic acid (except AUG, which is ordinarily the only codon for methionine; and UGG, which is ordinarily the only codon for tryptophan) can be modified to yield a functionally identical molecule. Accordingly, each silent variation of a nucleic acid which encodes a polypeptide of the present invention is implicit in each described polypeptide sequence and is within the scope of the present invention.

The term introduced in the context of inserting a nucleic acid into a cell, includes transfection or transformation or transduction and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA). When referring to introduction of a nucleotide sequence into a plant is meant to include transformation into the cell, as well as crossing a plant having the sequence with another plant, so that the second plant contains the heterologous sequence, as in conventional plant breeding techniques. Such breeding techniques are well known to one skilled in the art. For a discussion of plant breeding techniques, see Poehlman (1995) *Breeding Field Crops*. AVI Publication Co., Westport Conn., 4$^{th}$ Edit. Backcrossing methods may be used to introduce a gene into the plants. This technique has been used for decades to introduce traits into a plant. An example of a description of this and other plant breeding methodologies that are well known can be found in references such as Poelman, supra, and *Plant Breeding Methodology*, edit. Neal Jensen, John Wiley & Sons, Inc. (1988). In a typical backcross protocol, the original variety of interest (recurrent parent) is crossed to a second variety (nonrecurrent parent)

that carries the single gene of interest to be transferred. The resulting progeny from this cross are then crossed again to the recurrent parent and the process is repeated until a plant is obtained wherein essentially all of the desired morphological and physiological characteristics of the recurrent parent are recovered in the converted plant, in addition to the single transferred gene from the nonrecurrent parent.

By "promoter" is meant a regulatory region of DNA capable of regulating the transcription of a sequence linked thereto. It usually comprises a TATA box capable of directing RNA polymerase II to initiate RNA synthesis at the appropriate transcription initiation site for a particular coding sequence. The promoter is the minimal sequence sufficient to direct transcription in a desired manner. The term "regulatory region" is also used to refer to the sequence capable of initiating transcription in a desired manner. When referring to preferential expression, what is meant is expression at a higher level in the particular plant tissue than in other plant tissue. The present regulatory region confers expression preferentially in the pericarp. When referring to a pericarp preferred promoter or a promoter that expresses in a pericarp preferred manner is meant that it confers expression to an operably linked sequence to a higher degree in pericarp tissue than in other parts of the plant or seed.

As used herein, a nucleotide segment is referred to as operably linked when it is placed into a functional relationship with another DNA segment. For example, DNA for a signal sequence is operably linked to DNA encoding a polypeptide if it is expressed as a preprotein that participates in the secretion of the polypeptide; a promoter or enhancer is operably linked to a coding sequence if it stimulates the transcription of the sequence. Operably linked elements may be contiguous or non-contiguous. When used to refer to the joining of two protein coding regions, by operably linked it is intended that the coding regions are in the same reading frame. Alternatively, the additional gene(s) can be provided on multiple expression cassettes. Such an expression cassette is provided with a plurality of restriction sites and/or recombination sites for insertion of the polynucleotide to be under the transcriptional regulation of the regulatory regions.

The promoter of the invention may also be used in conjunction with another promoter. In one embodiment, the plant selection marker and the gene of interest can be both functionally linked to the same promoter. In another embodiment, the plant selection marker and the gene of interest can be functionally linked to different promoters. In yet third and fourth embodiments, the expression vector can contain two or more genes of interest that can be linked to the same promoter or different promoters. For example, the pericarp promoter described here can be used to drive the gene of interest and the selectable marker, or a different promoter used for one or the other. These other promoter elements can be those that are constitutive or sufficient to render promoter-dependent gene expression controllable as being cell-type specific, tissue-specific or time or developmental stage specific, or being inducible by external signals or agents. Such elements may be located in the 5' or 3' regions of the gene. Although the additional promoter may be the endogenous promoter of a structural gene of interest, the promoter can also be a foreign regulatory sequence. Promoter elements employed to control expression of product proteins and the selection gene can be any plant-compatible promoters. These can be plant gene promoters, such as, for example, the ubiquitin promoter (European patent application no. 0 342 926); the promoter for the small subunit of ribulose-1,5-bis-phosphate carboxylase (ss-RUBISCO) (Coruzzi et al., 1984; Broglie et al., 1984); or promoters from the tumor-inducing plasmids from *Agrobacterium tumefaciens*, such as the nopaline synthase, octopine synthase and mannopine synthase promoters (Velten and Schell, 1985) that have plant activity; or viral promoters such as the cauliflower mosaic virus (CaMV) 19S and 35S promoters (Guilley et al., 1982; Odell et al., 1985), the figwort mosaic virus FLt promoter (Maiti et al., 1997) or the coat protein promoter of TMV (Grdzelishvili et al., 2000). Alternatively, plant promoters such as heat shock promoters for example soybean hsp 17.5-E (Gurley et al., 1986); or ethanol-inducible promoters (Caddick et al., 1998) may be used. See International Patent Application No. WO 91/19806 for a review of illustrative plant promoters suitably employed in the present invention.

A promoter can additionally comprise other recognition sequences generally positioned upstream or 5' to the TATA box, referred to as upstream promoter elements, which influence the transcription initiation rate. It is recognized that having identified the nucleotide sequences for the promoter region disclosed herein, it is within the state of the art to isolate and identify further regulatory elements in the 5' region upstream from the particular promoter region identified herein. Thus the promoter region disclosed herein is generally further defined by comprising upstream regulatory elements such as those responsible for tissue and temporal expression of the coding sequence, enhancers and the like. In the same manner, the promoter elements, which enable expression in the desired tissue such as the pericarp can be identified, isolated, and used with other core promoters to confirm pericarp-preferred expression. By core promoter is meant the sequence sometimes referred to as the TATA box (or similar sequence), which is common to promoters in most genes encoding proteins. Thus the upstream promoter of the pericarp promoter can optionally be used in conjunction with its own or core promoters from other sources.

A construct is a package of genetic material inserted into the genome of a cell via various techniques.

As used herein, the term vector refers broadly to any plasmid or virus encoding an exogenous nucleic acid. The term should also be construed to include non-plasmid and non-viral compounds which facilitate transfer of nucleic acid into virions or cells, such as, for example, polylysine compounds and the like. The vector may be a viral vector that is suitable as a delivery vehicle for delivery of the nucleic acid, or mutant thereof, to a cell, or the vector may be a non-viral vector which is suitable for the same purpose.

Examples of viral and non-viral vectors for delivery of DNA to cells and tissues are well known in the art and are described, for example, in Ma et al. (1997, Proc. Natl. Acad. Sci. U.S.A. 94:12744-12746). Examples of viral vectors include, but are not limited to, a recombinant vaccinia virus, a recombinant adenovirus, a recombinant retrovirus, a recombinant adeno-associated virus, a recombinant avian pox virus, and the like (Cranage et al., 1986, EMBO J. 5:3057-3063; International Patent Application No. WO94/17810, published Aug. 18, 1994; International Patent Application No. WO94/23744, published Oct. 27, 1994). Examples of non-viral vectors include, but are not limited to, liposomes, polyamine derivatives of DNA, and the like.

In general, the methods available for construction of recombinant genes, optionally comprising various modifications for improved expression, can differ in detail. However, conventionally employed methods include PCR amplification, or the designing and synthesis of overlapping, complementary synthetic oligonucleotides, which are annealed and ligated together to yield a gene with convenient restriction sites for cloning, or subcloning from another already cloned source, or cloning from a library. The methods involved are standard methods for a molecular biologist (Sambrook et al., 1989).

One skilled in the art readily appreciates that the promoter can be used with any of a variety of nucleotide sequences comprising the gene of interest to be expressed in plants. For example, the gene of interest may encode a protein that is useful for industrial or pharmaceutical purposes or the like, or to impact the plant itself, such as through expression of a protein that provides disease resistance, insect resistance, herbicide resistance, or impacts agronomic traits as well as grain quality traits. The sequences used with the promoter can be native or non-native sequences to the plant. DNA sequences native to plants as well as non-native DNA sequences can be transformed into plants and used to modulate levels of native or non-native proteins.

The gene of interest can also be a nucleotide sequence used to target an area of the plant genome through homologous recombination. The promoter may be placed in a construct with such sequence, which sequence will not necessarily encode a protein. The sequence recombines in the genome and the promoter may be placed at the desired site targeted by the sequences to regulate the desired endogenous nucleotide sequence.

Further, the promoter can be used to drive mRNA that can be used for a silencing system, such as antisense, and in that instance, no protein is produced. Means of increasing or inhibiting a protein are well known to one skilled in the art and, by way of example, may include, transgenic expression, antisense suppression, co-suppression methods including but not limited to: RNA interference, gene activation or suppression using transcription factors and/or repressors, mutagenesis including transposon tagging, directed and site-specific mutagenesis, chromosome engineering and, homologous recombination. In the case of use with homologous recombination, no in vivo construct will be required.

Once the gene is engineered to contain desired features, such as the desired subcellular localization sequences, it may then be placed into an expression vector by standard methods. The selection of an appropriate expression vector will depend upon the method of introducing the expression vector into host cells. A typical expression vector contains prokaryotic DNA elements coding for a bacterial origin of replication and an antibiotic resistance gene to provide for the growth and selection of the expression vector in the bacterial host; a cloning site for insertion of an exogenous DNA sequence; eukaryotic DNA elements that control initiation of transcription of the exogenous gene (such as the promoter of the invention or another promoter); and DNA elements that control the processing of transcripts, such as transcription termination/polyadenylation sequences. It also can contain such sequences as are needed for the eventual integration of the vector into the plant chromosome.

Clearly, many variations in use of the promoter of the invention are available to one skilled in the art.

In addition, markers that facilitate identification of a plant cell containing the polynucleotide encoding the marker may be employed. Scorable or screenable markers are useful, where presence of the sequence produces a measurable product and can produce the product without destruction of the plant cell. Examples include a 62-glucuronidase, or uidA gene (GUS), which encodes an enzyme for which various chromogenic substrates are known (for example, U.S. Pat. Nos. 5,268,463 and 5,599,670); chloramphenicol acetyl transferase (Jefferson et al. (1987) *The EMBO Journal* vol. 6 No. 13 pp. 3901-3907); alkaline phosphatase. Other screenable markers include the anthocyanin/flavonoid genes in general (See discussion at Taylor and Briggs, (1990) *The Plant Cell* 2:115-127) including, for example, a R-locus gene, which encodes a product that regulates the production of anthocyanin pigments (red color) in plant tissues (Dellaporta et al., in *Chromosome Structure and Function*, Kluwer Academic Publishers, Appels and Gustafson eds., pp. 263-282 (1988)); the genes which control biosynthesis of flavonoid pigments, such as the maize C1 gene (Kao et al., (1996) *Plant Cell* 8: 1171-1179; Scheffler et al. (1994) *Mol. Gen. Genet.* 242:40-48) and maize C2 (Wienand et al., (1986) *Mol. Gen. Genet.* 203:202-207); the B gene (Chandler et al., (1989) *Plant Cell* 1:1175-1183), the p1 gene (Grotewold et al, (1991 *Proc. Natl. Acad. Sci. USA*) 88:4587-4591; Grotewold et al., (1994) *Cell* 76:543-553; Sidorenko et al., (1999) *Plant Mol. Biol.* 39:11-19); the bronze locus genes (Ralston et al., (1988) *Genetics* 119:185-197; Nash et al., (1990) *Plant Cell* 2(11): 1039-1049), among others. Yet further examples of suitable markers include the cyan fluorescent protein (CYP) gene (Bolte et al. (2004) *J. Cell Science* 117: 943-54 and Kato et al. (2002) *Plant Physiol* 129: 913-42), the yellow fluorescent protein gene (PhiYFP™ from Evrogen; see Bolte et al. (2004) *J. Cell Science* 117: 943-54); a lux gene, which encodes a luciferase, the presence of which may be detected using, for example, X-ray film, scintillation counting, fluorescent spectrophotometry, low-light video cameras, photon counting cameras or multiwell luminometry (Teeri et al. (1989) *EMBO J.* 8:343); a green fluorescent protein (GFP) gene (Sheen et al., (1995) *Plant J.* 8(5):777-84); and DsRed where plant cells transformed with the marker gene are red in color, and thus visually selectable (Dietrich et al. (2002) *Biotechniques* 2(2):286-293). Additional examples include a p-lactamase gene (Sutcliffe, (1978) *Proc. Nat'l. Acad. Sci. U.S.A.* 75:3737), which encodes an enzyme for which various chromogenic substrates are known (e.g., PADAC, a chromogenic cephalosporin); a xylE gene (Zukowsky et al., (1983) *Proc. Nat'l. Acad. Sci. U.S.A.* 80:1101), which encodes a catechol dioxygenase that can convert chromogenic catechols; an α-amylase gene (Ikuta et al., (1990) *Biotech.* 8:241); and a tyrosinase gene (Katz et al., (1983) *J. Gen. Microbiol.* 129:2703), which encodes an enzyme capable of oxidizing tyrosine to DOPA and dopaquinone, which in turn condenses to form the easily detectable compound melanin. Clearly, many such markers are available to one skilled in the art.

The expression vector can optionally also contain a signal sequence located between the promoter and the gene of interest and/or after the gene of interest. A signal sequence is a nucleotide sequence, translated to give an amino acid sequence, which is used by a cell to direct the protein or polypeptide of interest to be placed in a particular place within or outside the eukaryotic cell. Many signal sequences are known in the art. See, for example Becker et al., (1992) *Plant Mol. Biol.* 20:49, Knox, C., et al., "Structure and Organization of Two Divergent Alpha-Amylase Genes from Barley", *Plant Mol. Biol.* 9:3-17 (1987), Lerner et al., (1989) *Plant Physiol.* 91:124-129, Fontes et al., (1991) *Plant Cell* 3:483-496, Matsuoka et al., (1991) *Proc. Natl. Acad. Sci.* 88:834, Gould et al., (1989) *J. Cell. Biol.* 108:1657, Creissen et al., (1991) *Plant J.* 2:129, Kalderon, et al., (1984) "A short amino acid sequence able to specify nuclear location," *Cell* 39:499-509, Steifel, et al., (1990) "Expression of a maize cell wall hydroxyproline-rich glycoprotein gene in early leaf and root vascular differentiation" *Plant Cell* 2:785-793. When targeting the enzyme to the cell wall use of a signal sequence is necessary. One example is the barley alpha-amylase signal sequence. Rogers, J. C. (1985) "Two barley alpha-amylase gene families are regulated differently in aleurone cells" *J. Biol. Chem.* 260: 3731-3738.

Leader sequences can be included to enhance translation. The native leader sequence of PR3 may be used, or another leader sequence used, or no leader sequence used. Various available leader sequences may be substituted or added. Translation leaders are known in the art and include, for example: picornavirus leaders, for example, EMCV leader (encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165 (2):233-8); human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie. (1987) *Nucleic Acids Res.* 15(8):3257-73); and maize chlorotic mottle virus leader (MCMV) (Lommel et al. (1991) *Virology* 81:382-385). See also, Della-Cioppa et al. (1987) *Plant Physiology* 84:965-968.

In those instances where it is desirable to have the expressed product of the heterologous nucleotide sequence directed to a particular organelle, particularly the plastid, amyloplast, or to the endoplasmic reticulum, or secreted at the cell's surface or extracellularly, the expression cassette can further comprise a coding sequence for a transit peptide. Such transit peptides are well known in the art and include, but are not limited to, the transit peptide for the acyl carrier protein, the small subunit of RUBISCO, plant EPSP synthase, *Zea mays* Brittle-1 chloroplast transit peptide (Nelson et al. Plant Physiol 117(4):1235-1252 (1998); Sullivan et al. Plant Cell 3(12):1337-48; Sullivan et al., Planta (1995) 196(3):477-84; Sullivan et al., J. Biol. Chem. (1992) 267 (26):18999-9004) and the like. One skilled in the art will readily appreciate the many options available in expressing a product to a particular organelle. For example, the barley alpha amylase sequence is often used to direct expression to the cell wall (Rogers, J. Biol. Chem. 260:3731-3738 (1985)). Use of transit peptides is well known (e.g., see U.S. Pat. Nos. 5,717,084; 5,728,925). A protein may be targeted to the endoplasmic reticulum of the plant cell. This may be accomplished by use of a localization sequence, such as KDEL (SEQ ID NO: 11). This sequence (Lys-Asp-Glu-Leu (SEQ ID NO: 11)) contains the binding site for a receptor in the endoplasmic reticulum. (Munro et al., (1987) "A C-terminal signal prevents secretion of luminal ER proteins." *Cell.* 48:899-907. Retaining the protein in the vacuole is another example. Signal sequences to accomplish this are well known. For example, Raikhel U.S. Pat. No. 5,360,726 shows a vacuole signal sequence as does Warren et al at U.S. Pat. No. 5,889,174. Vacuolar targeting signals may be present either at the amino-terminal portion, (Holwerda et al., (1992) *The Plant Cell*, 4:307-318, Nakamura et al., (1993) *Plant Physiol.*, 101:1-5), carboxy-terminal portion, or in the internal sequence of the targeted protein. (Tague et al., (1992) *The Plant Cell*, 4:307-318, Saalbach et al. (1991) *The Plant Cell*, 3:695-708). Additionally, amino-terminal sequences in conjunction with carboxy-terminal sequences are responsible for vacuolar targeting of gene products (Shinshi et al. (1990) *Plant Molec. Biol.* 14:357-368).

In addition to a promoter, the expression cassette can include one or more enhancers. By "enhancer" is intended a cis-acting sequence that increases the utilization of a promoter. Such enhancers can be native to a gene or from a heterologous gene. Further, it is recognized that some promoters can contain one or more native, enhancers or enhancer-like elements. An example of one such enhancer is the 35S enhancer, which can be a single enhancer, or duplicated. See for example, McPherson et al, U.S. Pat. No. 5,322,938. Other methods known to enhance translation can also be utilized, for example, introns, and the like.

Where appropriate, the nucleotide sequence may be optimized for increased expression in the transformed plant. That is, nucleic acid sequences can be synthesized using plant-preferred codons for improved expression. See, for example, Campbell and Gowri (1990) *Plant Physiol.* 92: 1-11 for a discussion of host-preferred codon usage. Methods are available in the art for synthesizing plant-preferred genes. See, for example, U.S. Pat. Nos. 5,380,831, 5,436, 391, and Murray et al. (1989) *Nucl. Acids Res.* 17:477-498 (1989). Additional sequence modifications are known to enhance gene expression in a plant. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures. In another example, a Kozak or Kozak-like consensus sequence may be used to enhance translation, the full consensus sequence being (GCC)GCC A/G CC ATG G (SEQ ID NO: 12), with a purine (adenine or guanine) three bases upstream of the start codon. See, Kozak (1986) *Cell* 44(2):283-92; Kozak (1987) *Nucl. Acids Res.* 15(20):8125-8148.

The termination region can be native with the promoter nucleotide sequence of the present invention, can be native with the DNA sequence of interest, or can be derived from another source. Convenient termination regions are available from the Ti-plasmid of *A. tumefaciens*, such as the octopine synthase (MacDonald et al., (1991) *Nuc. Acids Res.* 19(20)5575-5581) and nopaline synthase termination regions (Depicker et al., (1982) *Mol. and Appl. Genet.* 1:561-573 and Shaw et al. (1984) *Nucleic Acids Research* Vol. 12, No. 20 pp 7831-7846 (nos)). Examples of various other terminators include the pin II terminator from the protease inhibitor II gene from potato (An, et al. (1989) *Plant Cell* 1, 115-122. See also, Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Obviously, many variations on the promoters, selectable markers, signal sequences, leader sequences, termination sequences, introns, enhancers and other components of the vector are available to one skilled in the art.

Methods for introducing expression vectors into plant tissue available to one skilled in the art are varied and will depend on the plant selected. Procedures for transforming a wide variety of plant species are well known and described throughout the literature. See for example, Miki and McHugh (2004); Klein et al. (1992); and Weising et al. (1988). For example, the DNA construct may be introduced into the genomic DNA of the plant cell using techniques such as microprojectile-mediated delivery (Klein et al. 1992), electroporation (Fromm et al., 1985), polyethylene glycol (PEG) precipitation (Mathur and Koncz, 1998), direct gene transfer (WO 85/01856 and EP-A-275 069), in vitro protoplast transformation (U.S. Pat. No. 4,684,611), and microinjection of plant cell protoplasts or embryogenic callus (Crossway, 1985). Co-cultivation of plant tissue with Agrobacterium tumefaciens is another option, where the DNA constructs are placed into a binary vector system (Ishida et al., 1996). The virulence functions of the Agrobacterium tumefaciens host will direct the insertion of the construct into the plant cell DNA when the cell is infected by the bacteria. See, for example, Fraley et al. (1983).

Standard methods for transformation of canola are described by Moloney et al. (1989). Corn transformation is described by Fromm et al. (1990), and Gordon-Kamm et al. (1990). Agrobacterium is primarily used in dicots, but certain monocots such as maize can be transformed by Agrobacterium. See, for example, U.S. Pat. No. 5,550,318. Rice transformation is described by Hiei et al. (1994), and Lee et al. (1991). Wheat can be transformed by techniques similar to those used for transforming corn or rice. Sorghum transformation is described by Casas et al. (1993) and barley transformation is described by Wan and Lemaux (1994). Soybean transformation is described in a number of publications, including U.S. Pat. No. 5,015,580.

In one method, the Agrobacterium transformation methods of Ishida et al. (1996) and also described in U.S. Pat. No. 5,591,616, are generally followed, with modifications that the inventors have found improve the number of transformants obtained. The Ishida method uses the A1188 variety of maize that produces Type I callus in culture. In one preferred embodiment the Hi II maize line is used which initiates Type II embryogenic callus in culture (Armstrong et al., 1991).

While Ishida recommends selection on phosphinothricin when using the bar or pat gene for selection, another preferred embodiment provides use of bialaphos instead. In general, as set forth in the U.S. Pat. No. 5,591,616, and as outlined in more detail below, dedifferentiation is obtained by culturing an explant of the plant on a dedifferentiation-inducing medium for not less than seven days, and the tissue during or after dedifferentiation is contacted with Agrobacterium having the gene of interest. The cultured tissue can be callus, an adventitious embryo-like tissue or suspension cells, for example. In this preferred embodiment, the suspension of Agrobacterium has a cell population of $10^6$ to $10^{11}$ cells/ml and are contacted for three to ten minutes with the tissue, or continuously cultured with Agrobacterium for not less than seven days. The Agrobacterium can contain plasmid pTOK162, with the gene of interest between border sequences of the T region of the plasmid, or the gene of interest may be present in another plasmid-containing Agrobacterium. The virulence region may originate from the virulence region of a Ti plasmid or Ri plasmid. The bacterial strain used in the Ishida protocol is LBA4404 with the 40 kb super binary plasmid containing three vir loci from the hypervirulent A281 strain. The plasmid has resistance to tetracycline. The cloning vector cointegrates with the super binary plasmid. Since the cloning vector has an E. coli specific replication origin, but not an Agrobacterium replication origin, it cannot survive in Agrobacterium without cointegrating with the super binary plasmid. Since the LBA4404 strain is not highly virulent, and has limited application without the super binary plasmid, the inventors have found in yet another embodiment that the EHA101 strain is preferred. It is a disarmed helper strain derived from the hypervirulent A281 strain. The cointegrated super binary/cloning vector from the LBA4404 parent is isolated and electroporated into EHA101, selecting for spectinomycin resistance. The plasmid is isolated to assure that the EHA101 contains the plasmid. EHA101 contains a disarmed pTi that carries resistance to kanamycin. See, Hood et al. (1986).

Further, the Ishida protocol as described provides for growing fresh culture of the Agrobacterium on plates, scraping the bacteria from the plates, and resuspending in the co-culture medium as stated in the U.S. Pat. No. 5,591,616 for incubation with the maize embryos. This medium includes 4.3 g MS salts, 0.5 mg nicotinic acid, 0.5 mg pyridoxine hydrochloride, 1.0 ml thiamine hydrochloride, casamino acids, 1.5 mg 2,4-D, 68.5 g sucrose and 36 g glucose per liter, all at a pH of 5.8. In a further preferred method, the bacteria are grown overnight in a 1 ml culture and then a fresh 10 ml culture is re-inoculated the next day when transformation is to occur. The bacteria grow into log phase, and are harvested at a density of no more than $OD_{600=0.5}$, preferably between 0.2 and 0.5. The bacteria are then centrifuged to remove the media and resuspended in the co-culture medium. Since Hi II is used, medium preferred for Hi II is used. This medium is described in considerable detail by Armstrong and Green (1985). The resuspension medium is the same as that described above. All further Hi II media are as described in Armstrong and Green (1985). The result is redifferentiation of the plant cells and regeneration into a plant. Redifferentiation is sometimes referred to as dedifferentiation, but the former term more accurately describes the process where the cell begins with a form and identity, is placed on a medium in which it loses that identity, and becomes "reprogrammed" to have a new identity. Thus the scutellum cells become embryogenic callus.

In accordance with the present invention, a transgenic plant is produced that contains an introduced pericarp promoter of the invention. It can be combined with any one of the components set forth above. In a preferred embodiment, the promoter is driving expression of a nucleotide sequence such that the sequence encodes a protein preferentially expressed in the pericarp of seed of the plant. Preferably, the plant is a cereal plant, and most preferably, a maize plant.

In a further embodiment, plant breeding can be used to introduce the nucleotide sequences into other plants once transformation has occurred. This can be accomplished by any means known in the art for breeding plants such as, for example, cross pollination of the transgenic plants that are described above with other plants, and selection for plants from subsequent generations which express the amino acid sequence. The plant breeding methods used herein are well known to one skilled in the art. For a discussion of plant breeding techniques, see Poehlman and Sleper (1995). Many crop plants useful in this method are bred through techniques that take advantage of the plant's method of pollination. A plant is self-pollinating if pollen from one flower is transferred to the same or another flower of the same plant. A plant is cross-pollinating if the pollen comes from a flower on a different plant. For example, in Brassica, the plant is normally self-sterile and can only be cross-pollinated unless, through discovery of a mutant or through genetic intervention, self-compatibility is obtained. In self-pollinating species, such as rice, oats, wheat, barley, peas, beans, soybeans, tobacco and cotton, the male and female plants are anatomically juxtaposed. During natural pollination, the male reproductive organs of a given flower pollinate the female reproductive organs of the same flower. Maize plants (Zea mays L.) can be bred by both self-pollination and cross-pollination techniques. Maize has male flowers, located on the tassel, and female flowers, located on the ear, on the same plant. It can self or cross-pollinate.

Pollination can be by any means, including but not limited to hand, wind or insect pollination, or mechanical contact between the male fertile and male sterile plant. For production of hybrid seeds on a commercial scale in most plant species pollination by wind or by insects is preferred. Stricter control of the pollination process can be achieved by using a variety of methods to make one plant pool male sterile, and the other the male fertile pollen donor. This can be accomplished by hand detassling, cytoplasmic male sterility, or control of male sterility through a variety of methods well known to the skilled breeder. Examples of more sophisticated male sterility systems include those described by Brar et al., U.S. Pat. Nos. 4,654,465 and 4,727,219 and Albertsen et al., U.S. Pat. Nos. 5,859,341 and 6,013,859.

Backcrossing methods may be used to introduce the gene into the plants. This technique has been used for decades to introduce traits into a plant. An example of a description of this and other plant breeding methodologies that are well known can be found in references such as Neal (1988). In a typical backcross protocol, the original variety of interest (recurrent parent) is crossed to a second variety (non-recurrent parent) that carries the single gene of interest to be transferred. The resulting progeny from this cross are then crossed again to the recurrent parent and the process is repeated until a plant is obtained wherein essentially all of the desired morphological and physiological characteristics of the recurrent parent are recovered in the converted plant, in addition to the single transferred gene from the non-recurrent parent.

EXAMPLES

The following is presented as illustrative of an embodiment of the invention and does not limit the scope of the invention as otherwise set forth.

Materials and Methods
Construction of Promoter-Reporter Gene Fusions and Introduction into Plants A sequence of 889 base pairs was identified and compared to known sequences. It was shown to have 100% identity to a portion of a 346,296 base pair 22 kDa zein gene cluster sequence Genbank accession number AF090447.2, "*Zea mays* 22 kDa alpha zein gene cluster, complete sequence" Mar. 14, 2003. The sequence also showed 99% identity to a portion of the 7343 base pair zein sequence at GenBank X61085.1, "*Z. mays* 22 kDa alpha-zein gene" Oct. 23, 2008 and 82% identity to the 78,101 base pair zein gene shown at GenBank accession No. AF031569.1 "*Zea mays* 22-kDa alpha zein gene cluster, complete sequence" Mar. 18, 2003. Small sections showed identity to GenBank accession number K02066.1 "Maize inbred line W22 zein (B49 subfamily) pseudogene Z7" Apr. 27, 1993, GenBank accession number BT016832.1 "*Zea mays* clone Contig665 mRNA sequence" Dec. 21, 2007, and NCBI accession number NM_001111589.1 "*Zea mays* 22 kD alpha zeins (az22z5), mRNA >gb/AF371277.1/AF371277 *Zea mays* alpha zein 5 mRNA, complte cds" Aug. 16, 2008.

The here cloned sequence was engineered for cloning purposes and fused to the β-glucoronidase (uidA, also referred to as GUS) reporter gene of *Escherichia coli* (Jefferson et al., 1987). The PR3884 bp sequence used is shown as SEQ ID NO. 2 and includes the native 5' leader sequence. As is apparent from the vector annotation, the construct included base 1114, which is the same as the native sequence, and base 1115, engineered for cloning purposes, and together is SEQ ID NO: 7. To ensure appropriate message termination, the potato proteinase inhibitor II (PinII) transcription terminator region was added 3' of the reporter genes for each fusion (An et al., 1989). These fusions were included on vectors that also carried the phosphinothricin N-acetyltransferase gene (pat) of *Streptomyces viridochromogenes* to confer herbicide resistance to transgenic plants. This gene confers resistance to bialaphos (Gordon-Kamm et al., 1990). The expression of the pat marker was controlled by the cauliflower mosaic virus 35S promoter and terminator sequences (Guilley et al., 1982; Odell et al., 1985). In addition, the vectors contained border sequences flanking the transcription units. These borders allowed the transformation of vector DNA enclosed within them into the target plant's genome. The vector is shown in FIG. 2.

The procedure for stable transformation was modified from that of Ishida et al. (1996) as described supra. Immature zygotic embryos from kernels of a Hi-II/elite line were transformed with *A. tumefaciens* strain EHA101 containing the relevant PR3 upstream sequence/reporter fusions to generate transgenic events. $T_0$ plants were regenerated from tissue culture of each event, transferred to soil in a greenhouse and pollinated using pollen from an elite inbred line to produce $T_1$ seeds.

Analysis of uidA Reporter Gene Expression in Transgenic Plant Tissues $T_1$ seeds were sectioned using a scalpel and were incubated with Jefferson's buffer containing 0.5 mgml$^{-1}$ X-gluc (Jefferson et al., 1987) for up to 16 hours at 37° C. until a clear blue stain was visible. In addition, $T_1$ seeds were allowed to germinate and the resulting $T_1$ seedlings were self-pollinated or pollinated with pollen from the non-transgenic Hill maize line. Representative tissue samples were collected from selected non-seed tissues and were incubated overnight at 37° C. with Jefferson's buffer containing 0.5 mgml$^{-1}$ X-gluc (Jefferson et al., 1987). Blue staining indicated GUS activity. Furthermore, developing $T_2$ seeds were harvested at 12 and 19 days after pollination and were similarly treated to reveal GUS activity, with sufficient incubation times to reveal any clear staining. Leaf tissue was harvested at 21 days post germination and at 12 days post-pollination. Stem, leaf, root, cob and silk were harvested at 12 days post-pollination and at 19 days post-pollination, and pollen and anther at pollen shed.

Figure 4:
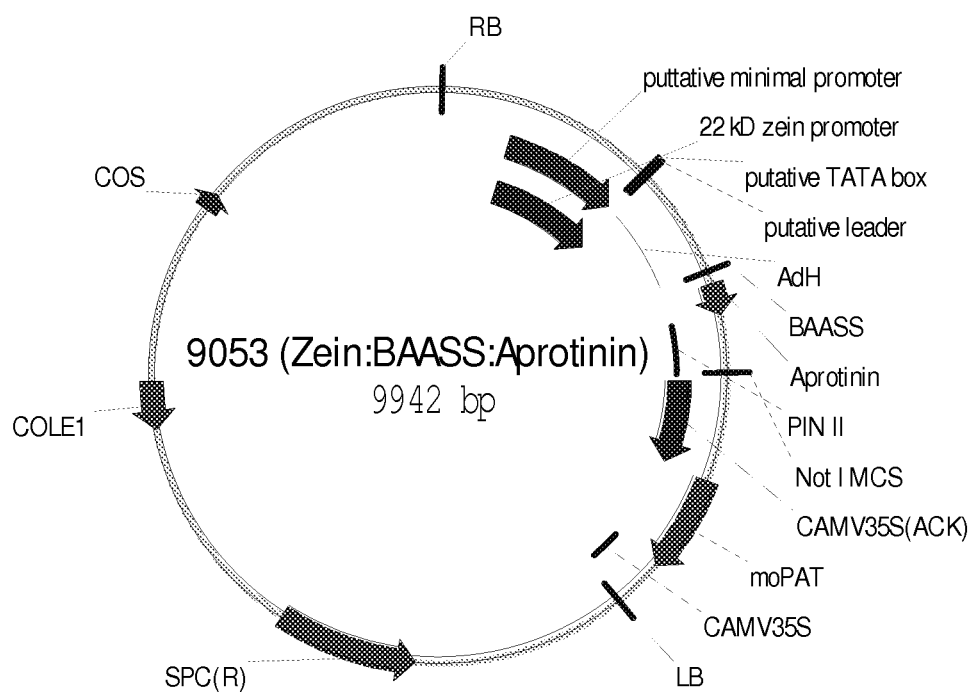
FIG. 4 is a diagram showing a vector map of a construct 9053, using the zein pericarp promoter without the 5' leader, driving expression of the aprotinin gene. The barley alpha amylase (BAASS) signal sequence with a pinII terminator is included. The selectable marker used in a maize optimized (moPAT) coding region drive by the 35S promoter and using the 35S terminator.

Transformation of Plants with Constructs Expressing Heterologous Protein and Driven by the PR3 Promoter A construct was prepared with the PR3 promoter driving a heterologous gene. A construct 9053 was prepared using the promoter to drive the aprotinin gene. The 866 bp PR3 sequence used is SEQ ID NO: 4. In this version the putative leader sequence of PR3 is truncated (SEQ ID NO: 6) and fused to the AdhI intron. The 787 bp minimal promoter used with construct 9053 has a slight variation at several bases relative to the sequence of GenBank accession No. AF090447.2 and is SEQ ID NO: 8. Expression of aprotinin in plants is described at Baszcyzynski et al. U.S. Pat. No. 5,824,870, incorporated herein by reference. FIG. 4 shows the map of 9053, including the promoter, the barley alpha amylase signal sequence (BAASS), the aprotinin gene, along with the pinII terminator. A maize optimized phosphinothricin acetyl transferase (pat) coding region was used as a selectable marker. Aprotinin was extracted as described in Example 3 of the '870 patent, incorporated herein by reference. Constructs with sequences encoding brazzein, laccase, and trypsinogen were also linked to the PR3 promoter. Expression of laccase in plants is described at U.S. Pat. No. 6,800,792 and, incorporated herein by reference.

Laccase was detected as described in Example 4 of the '792 patent. Expression of trypsinogen in plants is described at Example 1 of U.S. Pat. No. 6,087,558, incorporated herein by reference. Trypsinogen was assayed using procedures described in Example 4 of the '558 patent.

The PR3 promoter was determined to be capable of driving expression of an operably linked heterologous nucleotide sequence for aprotinin, brazzein, laccase and trypsinogen-encoding sequences expressed in plants.

Determination of PR3 as being Highly Expressed in the Plant Pericarp

As zein-expressing genes are expressed to the endosperm in Zea mays, it as expected that this sequence would be an endosperm-expressing promoter. See Woo et al. "Genomics analysis of genes expressed in maize endosperm identifies novel seed proteins and clarifies patterns of zein gene expression" Plant Cell Vol. 13, 2297-2317 (October 2001). Sequence encoding PR3 was discovered to be highly expressed not in the endosperm, but in the pericarp of seed. The promoter-uid reporter fusion was stably introduced into the maize genome by Agrobacterium mediated transformation. Following the transformation, uidA expression was analyzed in plant tissue, GUS activity was observed to be highly preferential in pericarp tissue in transformation experiments using the promoter-reporter fusion.

A Hill by SP122 cross was used for transformation of embryo tissue as described supra. Plants were then regenerated from transformation events obtained using the vector. A total of 112 plants were regenerated from 10 independent transformation events obtained using the PR3 promoter-uidA fusion with several plants from each event. Seed was harvested and dissected, and GUS expression observed.

Figure 3:
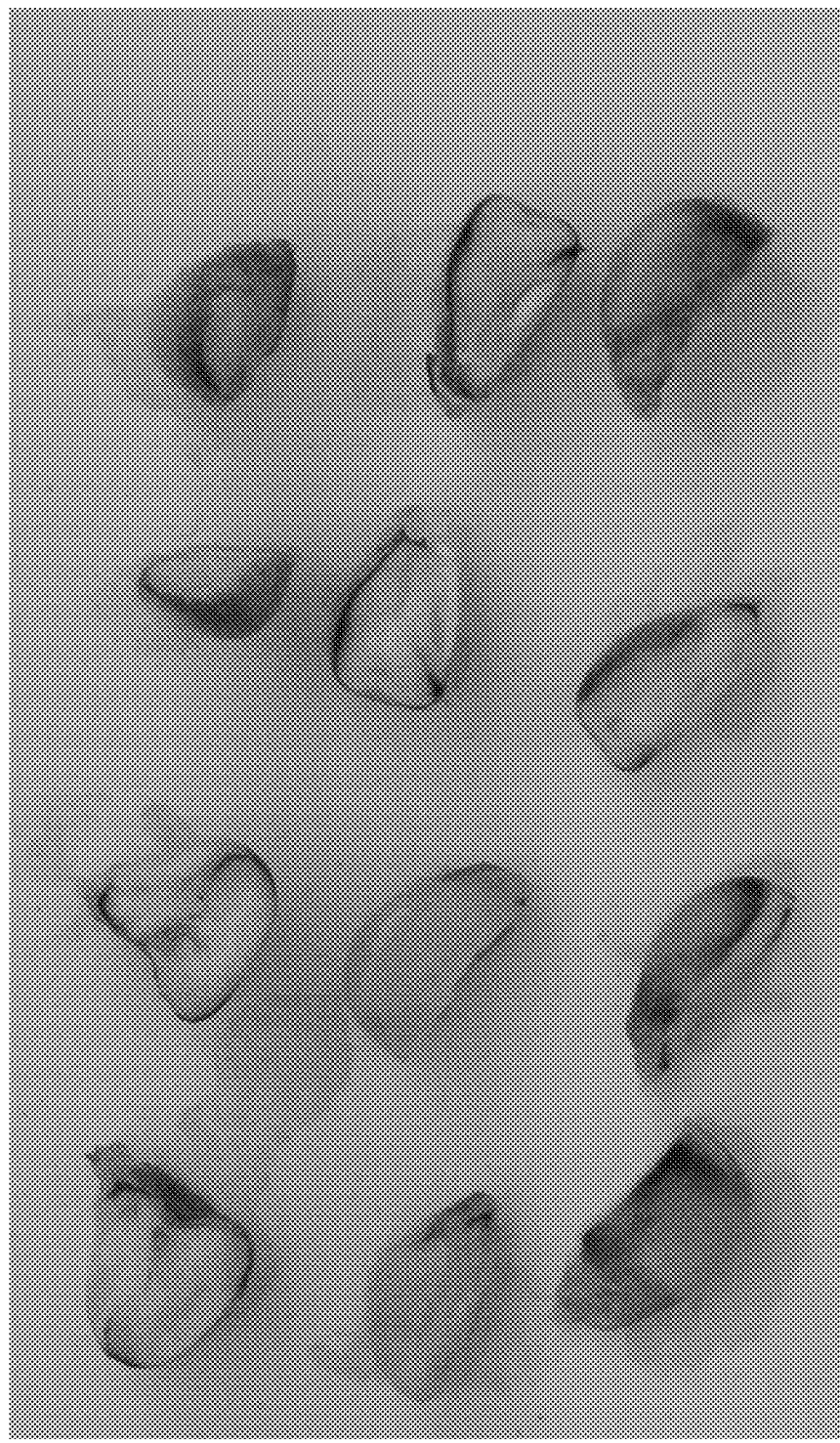
FIG. 3 is a black and white photograph of cross section staining results of plant seed tissue when expressing GUS with the pericarp promoter in event PMD 04 with the GUS staining shown by the darkened areas of pericarp tissue.

Seven events produced from transformation resulted in highly preferred pericarp expression, including event PMD 020, event PMD 030, event PMD 040, event PMD 070, event PMD 080, event PMD 090, and event PMD 100. PMD refers to the PR3-uid construct, the numbers that follow identify a specific event. The GUS expression for the transgenic seed are shown in FIG. 3 showing representative event PMD 040. As is evident in the Figure, GUS expressed strongly in the pericarp but not in endosperm, embryo or other portions of the seed. Further, observations of the plant prior to seed harvesting showed GUS did not express in other portions of the plant. Tissue from root, leaf, stem, cob, and silk tissue was examined and did not show significant staining except in a small portion of tissue at the junction of the cob with the developing kernel. In developing seeds, staining was not detected at twelve days after pollination but was observed in the pericarp at 19 days after pollination.

The PR3 promoter cloned here appears to have a high tissue specificity, with reporter gene expression being seed pericarp preferred. The strong highly pericarp preferred activity of the here cloned maize PR3 promoter makes it an excellent choice for pericarp preferred/specific expression in plants, preferably maize, and other cereals.

REFERENCES

Altschul, S. F., Gish, W., Miller, W., Myers, E. W. and Lipman, D. J. (1990) Basic local alignment search tool. J. Mol. Biol. 215, 403-410.

Altschul, S. F., Madden, T. L., Schaffer, A. A., Zhang, J., Zhang, Z., Miller, W. and Lipman, D. J. (1997) Nucleic Acids Res. 25, 3389-3402.

An, G., Mitra, A., Choi, H. K., Costa, M. A., An, K., Thornburg, R. W. and Ryan, C. A. (1989) Functional analysis of the 3' control region of the potato wound-inducible proteinase inhibitor II gene. Plant Cell 1, 115-122.

Anderson, E. (1944) Sources of effective germplasm in hybrid maize. Annals of the Missouri Botanical Garden 31, 355-361.

Armstrong, C. I. and Green, C. E. (1985) Establishment and maintenance of friable, embryogenic maize callus and involvement of L-proline. Planta 154, 207-214.

Armstrong, C., Green, C. and Phillips, R. (1991) Development and availability of germplasm with high type II culture response. Maize Genet. Coop. News Lett. 65, 92-93.

Ausubel F. M., Brent, R., Kingston, R. E., Moore, D. D., Seidman, J. G., Smith, J. A. and Struhl, K. (Eds.) (1993) Current Protocols in Molecular Biology, John Wiley & Sons, New York.

Bailey, M. R., Woodard, S. L., Callaway, E., Beifuss, K., Magallanes-Lundback, M., Lane, J. R., Horn, M. E., Mallubhotla, H., Delaney, D. D., Ward, M., Van Gastel, F., Howard, J. A. and Hood, E. E. (2004) Improved recovery of active recombinant laccase from maize seed. Appl. Microbiol. Biotechnol. 63, 390-397.

Becker, T. W., Templeman, T. S., Viret, J. F. and Bogorad, L. (1992) The cab-m7 gene: a light-inducible, mesophyll-specific gene of maize. Plant Mol. Biol. 20, 49-60.

Belanger, F. C. and Kriz, A. L. (1991) Molecular basis for allelic polymorphism of the maize globulin-1 gene. Genetics 129, 863-872.

Bradford, M. M. (1976) A rapid and sensitive method for the quantitation of microgram quantities of protein utilizing the principle of protein-dye binding. Anal. Biochem. 72, 248-254.

Brinch-Pedersen, H., Hatzack, F., Sorensen, L. D. and Holm, P. B. (2003) Concerted action of endogenous and heterologous phytase on phytic acid degradation in seed of transgenic wheat (Triticum aestivum L.). Transgenic Res. 12, 649-659.

Broglie, R., Coruzzi, G., Fraley, R. T., Rogers, S. G., Horsch, R. B., Niedermeyer, J. G., Fink, C. L. and Chua, N. H. (1984) Light-regulated expression of a pea ribulose-1,5-bisphosphate carboxylase small subunit gene in transformed plant cells. Science 224, 838-843.

Bustos, M. M., Guiltinan, M. J., Jordano, J., Begum, D., Kalkan, F. A. and Hall, T. C. (1989) Regulation of beta-glucuronidase expression in transgenic tobacco plants by an A/T-rich, cis-acting sequence found upstream of a French bean beta-phaseolin gene. Plant Cell 1, 839-853.

Caddick M. X., Greenland, A. J., Jepson, I., Krause, K. P., Qu, N., Riddell, K. V., Salter, M. G., Schuch, W., Sonnewald, U. and Tomsett, A. B. (1998) An ethanol inducible gene switch for plants used to manipulate carbon metabolism. Nat. Biotechnol. 16, 177-180.

Carrillo, C., Wigdorovitz, A., Oliveros, J. C., Zamorano, P. I., Sadir, A. M., Gomez, N., Salinas, J., Escribano, J. M. and Borca, M. V. (1998) Protective immune response to foot-and-mouth disease virus with VP1 expressed in transgenic plants. J. Virol. 72, 1688-1690.

Casas, A. M., Kononowicz, A. K., Zehr, U. B., Tomes, D. T., Axtell, J. D., Butler, L. G., Bressan, R. A. and Hasegawa P. M. (1993) Transgenic sorghum plants via microprojectile bombardment. Proc. Natl. Acad. Sci. USA 90, 11212-11216.

Chatterjee, M., Sparvoli, S., Edmunds, C., Garosi, P., Findlay, K. and Martin, C. (1996) DAG, a gene required for chloroplast differentiation and palisade development in Antirrhinum majus. EMBO J. 15, 4194-4207.

Christensen, A. H., Sharrock, R. A. and Quail, P. H. (1992) Maize polyubiquitin genes: structure, thermal perturbation of expression and transcript splicing, and promoter activity following transfer to protoplasts by electroporation. Plant Mol. Biol. 18, 675-689.

Cornejo, M. J., Luth, D., Blankenship, K. M., Anderson, O. D. and Blechl, A. E. (1993) Activity of a maize ubiquitin promoter in transgenic rice. Plant Mol. Biol. 23, 567-581.

Corpet, F. (1988) Multiple sequence alignment with hierarchical clustering. Nucleic Acids Res. 16, 10881-10890.

Coruzzi, G., Broglie, R., Edwards, C. and Chua, N. H. (1984) Tissue-specific and light-regulated expression of a pea nuclear gene encoding the small subunit of ribulose-1,5-bisphosphate carboxylase. EMBO J. 3, 1671-1679.

Creissen, G., Edwards, E. A., Enard, C., Wellburn, A. and Mullineaux, P. (1992) Molecular characterization of glutathione reductase cDNA from pea (Pisum sativum L.). Plant J. 2, 129-131.

Crossway, A. (1985) Mol. Gen. Genet. 202, 179-185.

Daniell, H., Streatfield, S. J. and Wycoff, K. (2001) Medical molecular farming: production of antibodies, biopharmaceuticals and edible vaccines in plants. Trends Plant Sci. 6, 219-226.

De Wilde, C., Van Houdt, H., De Buck, S., Angenon, G., De Jaeger, G. and Depicker, A. (2000) Plants as bioreactors for protein production: avoiding the problem of transgene silencing. Plant Mol. Biol. 43, 347-359.

Erlich, ed. (1989) PCR Technology (Stockton Press, New York).

Feinberg, A. P. and Vogelstein, B. (1983) A technique for radiolabeling DNA restriction endonuclease fragments to high specific activity. Anal. Biochem. 132, 6-13.

Fontes, E. B., Shank, B. B., Wrobel, R. L., Moose, S. P., OBrian, G. R., Wurtzel, E. T. and Boston, R. S. (1991) Characterization of an immunoglobulin binding protein homolog in the maize floury-2 endosperm mutant. Plant Cell 3, 483-496.

Fraley, R. T., Rogers, S. G., Horsch, R. B., Sanders, P. R., Flick, J. S., Adams, S. P., Bittner, M. L., Brand, L. A., Fink, C. L., Fry, J. S., Galluppi, G. R., Goldberg, S. B., Hoffmann, N. L. and Woo, S. C. (1983) Expression of bacterial genes in plant cells. Proc. Natl. Acad. Sci. USA, 80, 4803-4807.

Fromm, M., Taylor, L. P. and Walbot, V. (1985) Expression of genes transferred into monocot and dicot plant cells by electroporation. Proc. Natl. Acad. Sci. USA 82, 5824-5828.

Fromm, M. E., Morrish, F., Armstrong, C., Williams, R., Thomas, J. and Klein, T. M. (1990) Inheritance and expression of chimeric genes in the progeny of transgenic maize plants. Biotechnology (N Y) 8, 833-839.

Geffers, R., Cerff, R. and Hehl, R. (2000) Anaerobiosis-specific interaction of tobacco nuclear factors with cis-regulatory sequences in the maize GapC4 promoter. Plant Mol. Biol. 43, 11-21.

Gordon-Kamm, W., Dilkes, B. P., Lowe, K., Hoerster, G., Sun, X., Ross, M., Church, L., Bunde, C., Farrell, J., Hill, P., Maddock, S., Snyder, J., Sykes, L., Li, Z., Woo, Y. M., Bidney, D. and Larkins, B. A. (1990) Transformation of maize cells and regeneration of fertile transgenic plants. Plant Cell 2, 603-618.

Gould, S. J., Keller, G. A., Hosken, N., Wilkinson, J. and Subramani, S. (1989) A conserved tripeptide sorts proteins to peroxisomes. J. Cell. Biol. 108, 1657-1664.

Grdzelishvili, V. Z., Chapman, S. N., Dawson, W. O. and Lewandowski, D. J. (2000) Mapping of the tobacco mosaic virus movement protein and coat protein subgenomic RNA promoters in vivo. Virology 275, 177-192.

Gruber et al. (1993) Vectors for plant transformation. In: Glick, B. R. and Thompson J. E. (Eds.) Methods in Plant Molecular Biology and Biotechnology, CRC Press, pp. 89-119.

Guilley, H., Dudley, R. K., Jonard, G., Balazs, E. and Richards, K. E. (1982) Transcription of Cauliflower mosaic virus DNA: detection of promoter sequences, and characterization of transcripts. Cell 30, 763-773.

Gurley, W. B., Czarnecka, E., Nagao, R. T. and Key, J. L. (1986) Upstream sequences required for efficient expression of a soybean heat shock gene. Mol. Cell. Biol. 6, 559-565.

Haq, T. A., Mason, H. S., Clements, J. D. and Arntzen, C. J. (1995) Oral immunization with a recombinant bacterial antigen produced in transgenic plants. Science 268, 714-716.

Hiei, Y., Ohta, S., Komari, T. and Kumashiro, T. (1994) Efficient transformation of rice (Oryza sativs L.) mediated by Agrobacterium and sequence analysis of the boundaries of the T-DNA. Plant J. 6, 271-282.

Higgins, D. G. and Sharp, P. M. (1988) CLUSTAL: a package for performing multiple sequence alignment on a microcomputer. Gene 73, 237-244.

Higgins, D. G. and Sharp, P. M. (1989) Fast and sensitive multiple sequence alignments on a microcomputer. Comput. Appl. Biosci. 5, 151-153.

Hood, E. E., Helmer, G. L., Fraley, R. T. and Chilton, M. D. (1986) The hypervirulence of Agrobacterium tumefaciens A281 is encoded in a region of pTiBo542 outside of T-DNA. J. Bacteriol. 168, 1291-1301.

Hood, E. E., Witcher, D. R., Maddock, S., Meyer, T., Baszczynski, C., Bailey, M., Flynn, P., Register, J., Marshall, L., Bond, D., Kulisek, E., Kusnadi, A., Evangelista, R., Nikolov, Z., Wooge, C., Mehigh, R. J., Hernan, R., Kappel, W. K., Ritland, D., Li, C-P. and Howard, J. A. (1997) Commercial production of avidin from transgenic maize: characterization of transformant, production, processing, extraction and purification. Mol. Breed. 3, 291-306.

Hood, E. E., Woodard, S. L. and Horn, M. E. (2002) Monoclonal antibody manufacturing in transgenic plants—myths and realities. Curr. Opin. Biotechnol. 13, 630-635.

Hood, E. E., Bailey, M. R., Beifuss, K., Magallanes-Lundback, M., Horn, M. E., Callaway, E., Drees, C., Delaney, D. E., Clough, R. and Howard, J. A. (2003) Criteria for high-level expression of a fungal laccase gene in transgenic maize. Plant Biotechnol. J. 1, 129-140.

Huang, X., Miller, W., Schwartz, S, and Hardison, R. C. (1992) Parallelization of a local similarity algorithm. Comput. Appl. Biosci. 8, 155-65.

Innis, M., Gelfand, D., Sninsky, J. and White, T. (1990) PCR Protocols: A Guide to Methods and Applications. Academic Press, New York.

Innis, M., Gelfand, D. and Sninsky, J. (1995) PCR Strategies. Academic Press, New York.

Innis, M., Gelfand, D. and Sninsky, J. (1999) PCR Applications: Protocols for Functional Genomics. Academic Press, New York.

Ishida, Y., Saito, H., Ohta, S., Hiei, Y., Komari, T. and Kumashiro, T. (1996) High efficiency transformation of maize (Zea mays L.) mediated by Agrobacterium tumefaciens. Nat. Biotechnol. 14, 745-750.

Jefferson, R. A., Kavanagh, T. A. and Bevan, M. W. (1987) GUS fusions: beta-glucuronidase as a sensitive and versatile gene fusion marker in higher plants. EMBO J. 6, 3901-7.

Kalderon, D., Roberts, B. L., Richardson, W. D. and Smith A. E. (1984) A short amino acid sequence able to specify nuclear location. Cell 39, 499-509.

Karlin, S, and Altschul, S. F. (1990) Methods for assessing the statistical significance of molecular sequence features by using general scoring schemes. Proc. Natl. Acad. Sci. USA 87, 2264-2268.

Karlin, S, and Altschul, S. F. (1993) Applications and statistics for multiple high-scoring segments in molecular sequences. Proc. Natl. Acad. Sci. USA 90, 5873-5877.

Klein, T. M., Arentzen, R., Lewis, P. A. and Fitzpatrick-McElligott, S. (1992) Transformation of microbes, plants and animals by particle bombardment. Biotechnology (N Y) 10, 286-291.

Lamphear, B. J., Streatfield, S. J., Jilka, J. M., Brooks, C. A., Barker, D. K., Turner, D. D., Delaney, D. E., Garcia, M., Wiggins, W., Woodard, S. L., Hood, E. E., Tizard, I. R., Lawhorn, B. and Howard, J. A. (2002) Delivery of subunit vaccines in maize seed. J. Control. Release 85, 169-180.

Lee, N., Wang, Y., Yang, J., Ge, K., Huang, S., Tan, J. and Testa, D. (1991) Efficient transformation and regeneration of rice small cell groups. Proc. Nat. Acad. Sci. USA 88, 6389-6393.

Lessard, P. A., Kulaveerasingam, H., York, G. M., Strong, A. and Sinskey, A. J. (2002) Manipulating gene expression for the metabolic engineering of plants. Metab. Eng. 4, 67-79.

Leung, J., Fukuda, H., Wing, D., Schell, J. and Masterson, R. (1991) Functional analysis of cis-elements, auxin response and early developmental profiles of the mannopine synthase bi-directional promoter. Mol. Gen. Genet. 230, 463-474.

Maiti, I. B., Gowda, S., Kiernan, J., Ghosh, S. K. and Shepherd, R. J. (1997) Promoter/leader deletion analysis and plant expression vectors with the figwort mosaic virus (FMV) full length transcript (FLt) promoter containing single or double enhancer domains. Transgenic Res. 6, 143-156.

Mason, H. S., Lam, D. M. and Arntzen, C. J. (1992) Expression of hepatitis B surface antigen in transgenic plants. Proc. Natl. Acad. Sci. USA 89, 11745-11749.

Mathur, J. and Koncz, C. (1998) PEG-mediated protoplast transformation with naked DNA. Methods Mol. Biol. 82, 267-276.

Matsuoka, K. and Nakamura, K. (1991) Propeptide of a precursor to a plant vacuolar protein required for vacuolar targeting. Proc. Natl. Acad. Sci. USA 88, 834-838.

Meinkoth, J. and Wahl, G. (1984) Hybridization of nucleic acids immobilized on solid supports. Anal. Biochem. 138, 267-284.

Miki, B. and McHugh, S. (2004) Selectable marker genes in transgenic plants: applications, alternatives and biosafety. J. Biotechnol. 107, 193-232.

Moloney, M. et al. (1989) High efficiency transformation of *Brassica napus* using *Agrobacterium* vectors. Plant Cell Reports 8, 238-242.

Mullis et al. (1987) Methods Enzymol. 155:335-350 Myers, E. W. and Miller, W. (1988) Optimal alignments in linear space. Comput. Appl. Biosci. 4, 11-17.

Needleman, S. B. and Wunsch, C. D. (1970) A general method applicable to the search for similarities in the amino acid sequence of two proteins. J. Mol. Biol. 48, 443-453.

Nessler, C. L. (1994) Metabolic engineering of plant secondary products. Transgenic Res. 3, 109-115.

Neuhausen, S. (1989) A survey of Iowa Stiff Stalk parents derived inbreds and BSSS(HT)C5 using RFLP analysis. MNL 63, 110-111.

Odell, J. T., Nagy, F. and Chua, N. H. (1985) Identification of DNA sequences required for activity of the cauliflower mosaic virus 35S promoter. Nature 313, 810-812.

Oldach, K. H., Becker, D. and Lorz, H. (2001) Heterologous expression of genes mediating enhanced fungal resistance in transgenic wheat. Mol. Plant. Microbe Interact. 14, 832-838.

Pearson, W. R. and Lipman, D. J. (1988) Improved tools for biological sequence comparison. Proc. Natl. Acad. Sci. USA 85, 2444-2448.

Pearson, W. R. (1994) Using the FASTA program to search protein and DNA sequence databases. Methods Mol. Biol. 24, 307-331.

Poehlman, J. M. and Sleper, D. A. (1995) Breeding field crops, 4$^{th}$ Edition, Iowa State University Press.

Poirier, Y., Nawrath, C. and Somerville, C. (1995) Production of polyhydroxyalkanoates, a family of biodegradable plastics and elastomers, in bacteria and plants. Biotechnology (N Y) 13, 142-150.

Rogers, J. C. (1985) Two barley alpha-amylase gene families are regulated differently in aleurone cells. J. Biol. Chem. 260, 3731-3738.

Roussell, D. L., Boston, R. S., Goldsbrough, P. B. and Larkins, B. A. (1988) Deletion of DNA sequences flanking an Mr 19,000 zein gene reduces its transcriptional activity in heterologous plant tissues. Mol. Gen. Genet. 211, 202-209.

Russell, D. A. and Fromm, M. E. (1997) Tissue-specific expression in transgenic maize of four endosperm promoters from maize and rice. Transgenic Res. 6, 157-168.

Sambrook, J., Fritsch, E. F. and Maniatis, T. (1989) Molecular Cloning: A Laboratory Manual, 2$^{nd}$ Edition. Cold Spring Harbor Laboratory Press, Plainview, N. Y.

Smith, T. F. and Waterman, M. S. (1981) Adv. Appl. Math. 2, 482-489.

Stacey, J. and Issac, P. G. (1994) Isolation of DNA from plants. Methods Mol. Biol. 28, 9-15.

Sprague, G. F. (1946) Early testing of inbred lines of maize. J. Amer. Soc. Agron. 38, 108-117.

Stiefel, V., Ruiz-Avila, L., Raz, R., Pilar Valles, M., Gomez, J., Pages, M., Martinez-Izquierdo, J. A., Ludevid, M. D., Langdale, J. A., Nelson, T., et al. (1990) Expression of a maize cell wall hydroxyproline-rich glycoprotein gene in early leaf and root vascular differentiation. Plant Cell 2, 785-793.

Streatfield, S. J., Jilka, J. M., Hood, E. E., Turner, D. D., Bailey, M. R., Mayor, J. M., Woodard, S. L., Beifuss, K., Horn, M. E., Delaney, D. E., Tizard, I. R. and Howard, J. A. (2001) Plant-based vaccines: unique advantages. Vaccine 19, 2742-2748.

Streatfield, S. J., Mayor, J. M., Barker, D. K., Brooks, C., Lamphear, B. J., Woodard, S. L., Beifuss, K. K., Vicuna, D. V., Massey, L. A. Massey, Horn, M. E., Delaney, D. D., Nikolov, Z. L., Hood, E. E., Jilka, J. M. and Howard, J. A. (2002) Development of an edible subunit vaccine in corn against enterotoxigenic strains of *Escherichia coli*. In Vitro Cell. Dev. Biol.-Plant 38, 11-17.

Streatfield, S. J., Lane, J. R., Brooks, C. A., Barker, D. K., Poage, M. L., Mayor, J. M., Lamphear, B. J., Drees, C. F., Jilka, J. M., Hood, E. E. and Howard, J. A. (2003) Corn as a production system for human and animal vaccines. Vaccine 21, 812-815.

Takimoto, I., Christensen, A. H., Quail, P. H., Uchimiya, H. and Toki, S. (1994) Non-systemic expression of a stress-response maize polyubiquitin gene (Ubi-1) in transgenic rice plants. Plant Mol. Biol. 26, 1007-1012.

Velten, J. and Schell, J. (1985) Selection-expression plasmid vectors for use in genetic transformation of higher plants. Nucleic Acids Res. 13, 6981-6998.

Vilardell, J., Mundy, J., Stilling, B., Leroux, B., Pla, M., Freyssinet, G. and Pages, M. (1991) Regulation of the maize rab 17 gene promoter in transgenic heterologous systems. Plant Mol. Biol. 17, 985-993.

Wallace, N. H. and Kriz, A. L. (1991) Nucleotide sequence of a cDNA clone corresponding to the maize globulin-2 gene. Plant Physiol. 95, 973-975.

Wan, Y. and Lemaux, P. G. (1994) Generation of large numbers of independently transformed fertile barley plants. Plant Physiol. 104, 37-48.

Waterhouse, P. M., Wang, M. B. and Lough, T. (2001) Gene silencing as an adaptive defense against viruses. Nature 411, 834-842.

Weigel, D. and Nilsson, O. (1995) A developmental switch sufficient for flower initiation in diverse plants. Nature 377, 495-500.

Weising, K., Schell, J. and Kahl, G. (1988) Foreign genes in plants: transfer, structure, expression, and applications. Annu. Rev. Genet. 22, 421-477.

Wohlleben, W., Arnold, W., Broer, I., Hillemann, D., Strauch, E. and Puhler, A. (1988) Nucleotide sequence of the phosphinothricin N-acetyltransferase gene from *Streptomyces virochromogenes* Tu494 and its expression in *Nicotiana tabacum*. Gene 70, 25-37.

Woodard, S. L., Mayor, J. M., Bailey, M. R., Barker, D. K., Love, R. T., Lane, J. R., Delaney, D. E., McComas-Wagner, J. M., Mallubhotla, H. D., Hood, E. E., Dangott, L. J., Tichy, S. E. and Howard, J. A. (2003) Maize-derived bovine trypsin: characterization of the first large-scale, commercial protein product from transgenic plants. Biotechnol. Appl. Biochem. 38, 123-130.

Yang, N. S. and Russell, D. (1990) Maize sucrose synthase-1 promoter drives phloem cell-specific expression of GUS gene in transgenic tobacco plants. Proc. Natl. Acad. Sci. USA 87, 4144-4148.

Ye, X., Al-Babili, S., Kloti, A., Zhang, J., Lucca, P., Beyer, P. and Potrykus, I. (2000) Engineering the provitamin A (beta-carotene) biosynthetic pathway into (carotenoid-free) rice endosperm. Science 287, 303-305.

Yu, H. and Kumar, P. P. (2003) Post-transcriptional gene silencing in plants by RNA. Plant Cell Rep. 22, 167-174.

Zhong, G-Y, Peterson, D., Delaney, D. E., Bailey, M., Witcher, D. R., Register, J. C. (III), Bond, D., Li, C-P., Marshall, L., Kulisek, E., Ritland, D., Meyer, T., Hood, E. E. and Howard, J. A. (1999) Commercial production of aprotinin in transgenic maize seeds. Mol. Breed. 5, 345-356.

Summary of Sequence Identifiers:
SEQ ID NO: 1, the 787 bp minimal promoter of PR3
SEQ ID NO: 2, the PR3884 bp promoter and 5' leader sequence
SEQ ID NO: 3, the 889 bp PR3 promoter, 5' leader sequence, ATG start site (FIG. 1)
SEQ ID NO: 4, the PR3866 bp promoter
SEQ ID NO: 5, the PR368 bp putative leader sequence
SEQ ID NO: 6, the PR348 bp truncated putative leader sequence
SEQ ID NO: 7, the PR3 promoter of construct 9071 including bases 230-1115
SEQ ID NO: 8, the PR3787 bp minimal promoter of construct 9053
SEQ ID NO: 9, the sequence of construct 9071
SEQ ID NO: 10, the sequence of construct 9053

Sequences Used in Construct 9071 (SEQ ID NO: 9) Using Zein Pericarp Promoter Driving Expression of GUS
Right border—1-25
PR3 22kD zein promoter+5' leader—230-1113 (SEQ ID NO: 2)
PR3 promoter—230-1016 (SEQ ID NO: 1)
putative TATA Box—1017-1023
putative leader sequence—1048-1115 (SEQ ID NO: 5)
GUS PolyHis—1116-2945
PinII terminator—2951-3271
CaMV35S promoter—3327-3868
moPAT coding region—3889-4440
CaMV35S terminator—4460-4661
spectinomycin resistance coding region—5921-6709
streptomycin resistance coding region—6767-7291
Left border—4721-4745
COS—9267-9367
COLE—7984-8253

Sequences Used in Construct 9053 (SEQ ID NO: 10) Using Zein Pericarp Promoter Driving Expression of Aprotinin
Right border—1-25
PR322 kD zein promoter—440-1305 (SEQ ID NO: 4)
PR3 promoter—440-1226 (SEQ ID NO: 8)
Putative TATA Box—1227-1233
Truncated putative leader sequence-1258-1305 (SEQ ID NO: 6)
ADH intron—1306-1863
BAASS—1881-1952
Aprotinin—1953-2132
PinII terminator—2138-2458
CaMV35S promoter—2562-3043
moPAT coding region—3064-3615
CaMV35S terminator—3634-3836
spectinomycin resistance coding region—5096-5884
Left border—3896-3920
COS—8442-8542
COLE—7159-7428

What is claimed is:

1. A method for preferentially expressing a nucleic acid molecule in plant seed pericarp tissue, the method comprising:
   (a) transforming a plant cell with an expression cassette comprising a regulatory region consisting essentially of SEQ ID NO: 1 or SEQ ID NO: 8;
   (b) said regulatory region operably linked to said nucleic acid molecule; and
   (c) detecting transcription of said operably linked nucleic acid molecule to a higher degree in said pericarp of said seed than in endosperm of said seed.

2. The method of claim 1, wherein said regulatory region comprises SEQ ID NO: 1.

3. The method of claim 1, wherein said nucleic acid molecule produces a measurable product which may be detected in said pericarp tissue.

4. The method of claim 3, further comprising visually detecting the presence of said measurable product in said pericarp tissue.

5. The method of claim 3, wherein said product comprises a detectable color.

6. The method of claim 1, wherein said nucleic acid molecule produces a product which changes the composition of said pericarp tissue compared to the composition of said pericarp tissue prior to expression of said nucleic acid molecule.

7. The method of claim 1, further comprising selecting said nucleic acid molecule such that said molecule produces a product which changes the composition of said pericarp tissue compared to the composition of said pericarp tissue prior to expression of said nucleic acid molecule.

8. The method of claim 1, further comprising introducing said expression cassette into at least one plant cell, producing at least one plant producing a plurality of seed, and physically separating seed in said plurality comprising said nucleic acid molecule from seed in said plurality not comprising said nucleic acid molecule, by detecting the presence or absence of said nucleic acid molecule or product produced by said nucleic acid molecule in pericarp tissue of said seed.

9. A plant or plant part comprising a seed, said plant or plant part comprising a heterologous nucleic acid molecule operably linked to a regulatory region consisting essentially of SEQ ID NO: 1 or SEQ ID NO: 8 wherein expression of said heterologous nucleic acid molecule is detected at a higher level in pericarp tissue of seed of said plant than in endosperm tissue of said seed.

10. The plant or plant part of claim 9, wherein said plant or plant part comprises pericarp tissue, said nucleic acid molecule producing a product which changes the composition of said pericarp tissue compared to the composition of said pericarp tissue prior to expression of said nucleic acid molecule.

11. The plant or plant part of claim 9, wherein said nucleic acid molecule produces a product which changes the color of said pericarp tissue.

12. The plant or plant part of claim 9, wherein said nucleic acid molecule produces a product which changes the molecular characteristics or expression of a nucleic acid or amino acid molecule in said pericarp tissue.

13. An isolated regulatory region consisting of SEQ ID NO: 1 or SEQ ID NO: 8 operably linked to a heterologous nucleic acid molecule.

14. A vector comprising an isolated regulatory region consisting essentially of SEQ ID NO: 1 or SEQ ID NO: 8 operably linked to a heterologous nucleic acid molecule.

15. A method for preferentially expressing a nucleic acid molecule in plant seed pericarp tissue, the method comprising:
    (a) transforming a plant cell with an expression cassette comprising a regulatory region comprising SEQ ID NO: 1 or SEQ ID NO: 8;
    (b) said regulatory region operably linked to a heterologous promoter and a nucleic acid molecule; and
    (c) detecting transcription of said operably linked nucleic acid molecule in said pericarp.

* * * * *